United States Patent [19]
Takahashi et al.

[11] Patent Number: 5,155,941
[45] Date of Patent: Oct. 20, 1992

[54] INDUSTRIAL ENDOSCOPE SYSTEM HAVING A ROTARY TREATMENT MEMBER

[75] Inventors: Ichiro Takahashi, Hachioji; Minoru Okada, Sagamihara; Satoshi Tatami, Tama; Tsutomu Yamamoto, Hachioji; Masahiro Kumakura, Zama; Hideki Okuwa, Hachioji; Hiroaki Noda, Hachioji; Nobuyuki Sakamoto, Hachioji; Tatsuya Ito, Akikawa; Eiichi Fuse, Hachioji; Masaaki Hayashi, Hachioji; Katsuya Suzuki, Hachioji, all of Japan

[73] Assignee: Olympus Optical Co., Ltd., Tokyo, Japan

[21] Appl. No.: 584,947

[22] Filed: Sep. 18, 1990

[30] Foreign Application Priority Data

Sep. 18, 1989 [JP] Japan .................................. 1-242860
Apr. 18, 1990 [JP] Japan .................................. 2-102387

[51] Int. Cl.⁵ .............................................. B24B 49/00
[52] U.S. Cl. ................................ 51/165.72; 51/170 T; 51/134.5 R; 408/16; 409/143
[58] Field of Search ............... 51/165.72, 281 P, 322, 51/326, 327, 134.5 R, 259, 170 T, 170 MT; 408/16; 409/133; 73/116; 350/26, 96, 574; 356/241

[56] References Cited

U.S. PATENT DOCUMENTS

| 4,577,388 | 3/1986 | Wood .................................. 409/143 |
| 4,640,124 | 2/1987 | Diener et al. . |
| 4,659,195 | 4/1987 | D'Amelio et al. . |
| 4,696,544 | 9/1987 | Costella . |
| 4,701,988 | 10/1987 | Wood .................................. 409/143 |
| 4,784,117 | 11/1988 | Miyazaki . |
| 4,784,463 | 11/1988 | Miyazaki . |

FOREIGN PATENT DOCUMENTS

| 636061 | 6/1934 | Fed. Rep. of Germany ........ 408/16 |
| 83949 | 5/1983 | Japan . |
| 58-162924 | 9/1983 | Japan . |
| 975236 | 11/1982 | U.S.S.R. .................................. 408/16 |
| 868176 | 5/1961 | United Kingdom .................. 408/16 |

OTHER PUBLICATIONS

Hovnanian–Fibre Optic Dental Television Monitor and Floroscope — 1960.

Primary Examiner—M. Rachuba
Attorney, Agent, or Firm—Armstrong & Kubovcik

[57] ABSTRACT

Disclosed is an industrial endoscope system having a rotary treatment member, attached to a hard top part at a distal end of an insertion unit, for effecting a treatment such as grinding by rotating this treatment member itself. The system includes a moving means for making a distal end of the treatment member movable in the axial directions of the insertion unit. This easily leads the treatment member to a target position via a lead-in port of an engine; or the treatment member can be set in a position suitable for the treatment.

23 Claims, 21 Drawing Sheets

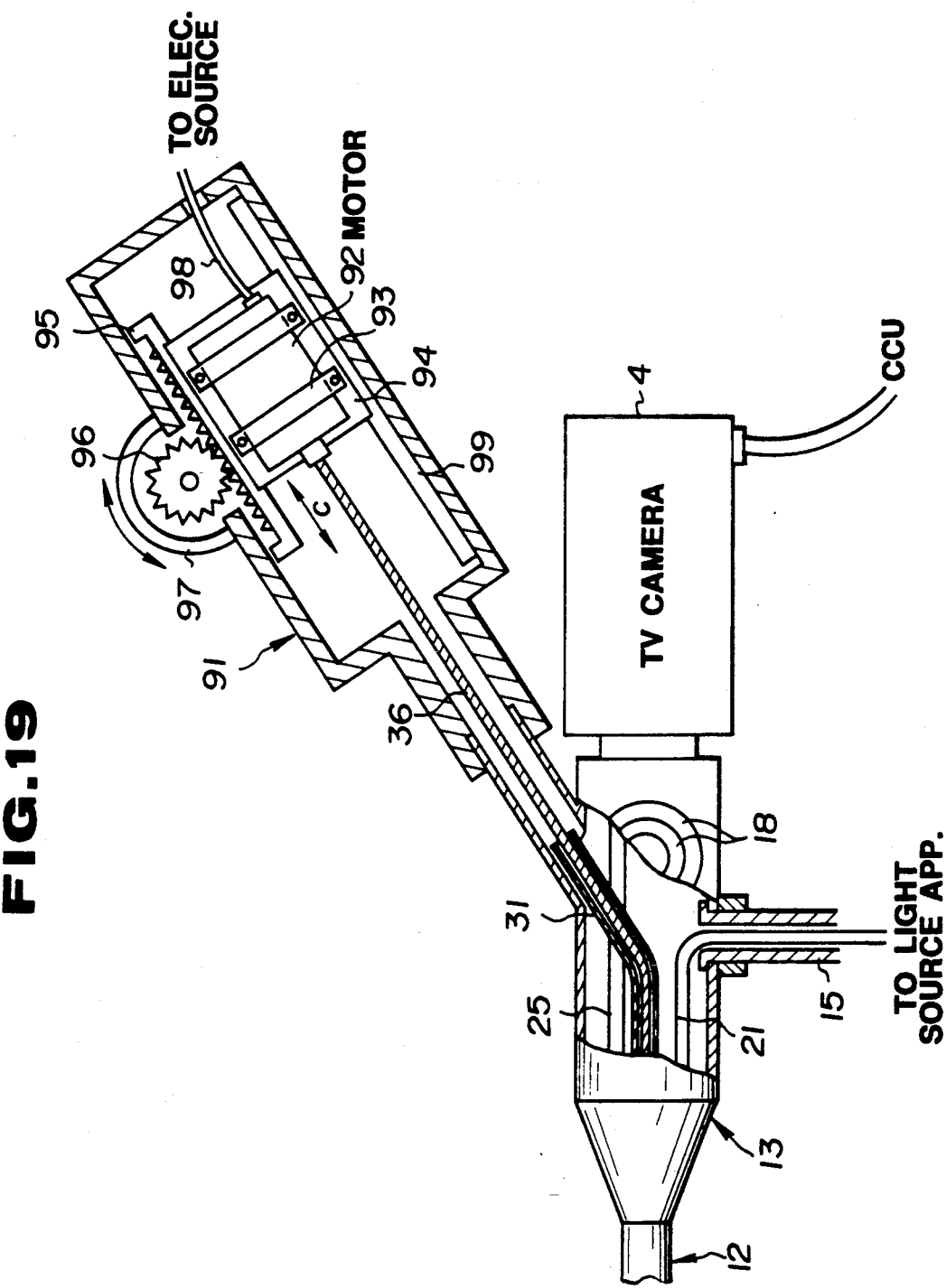

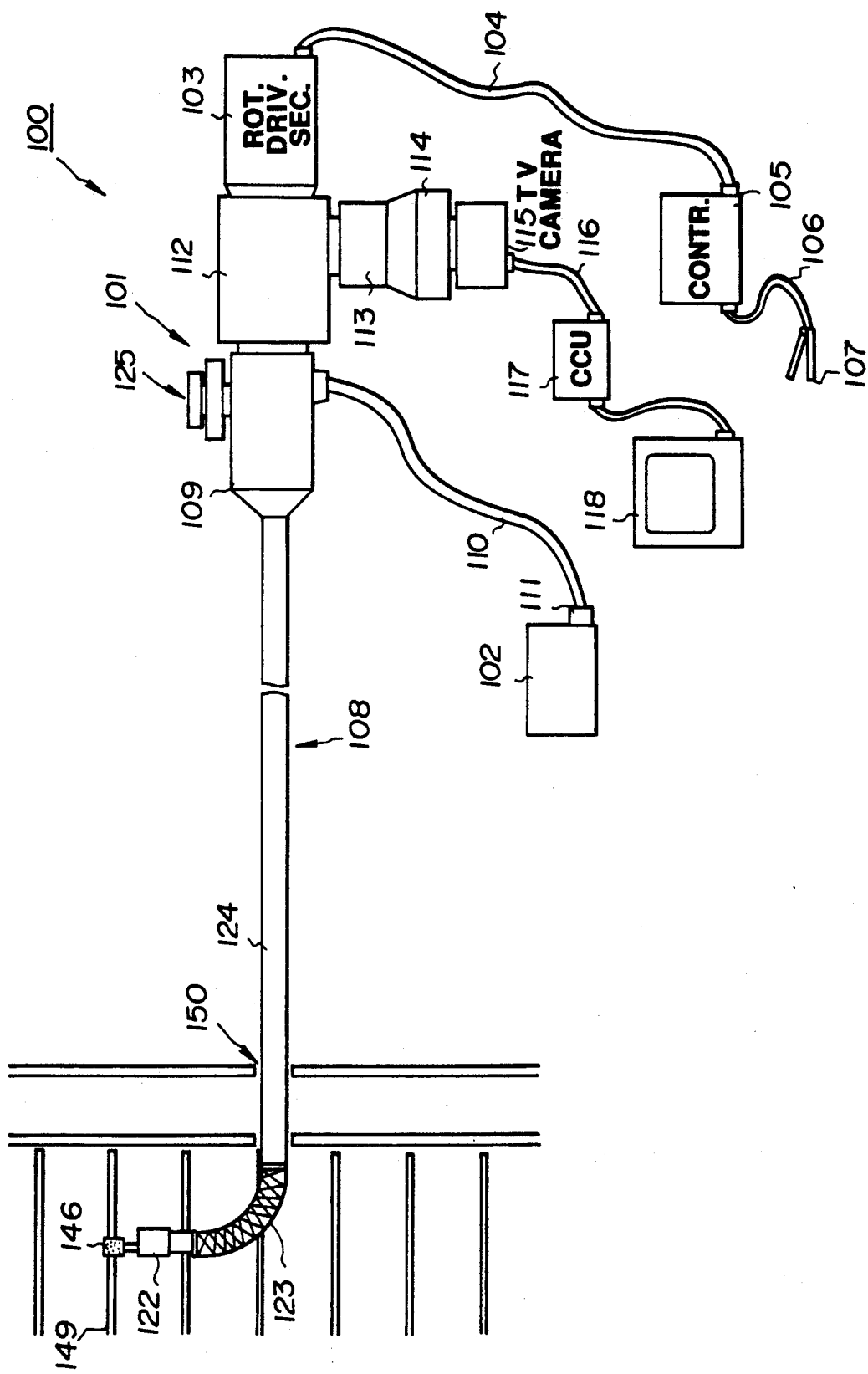

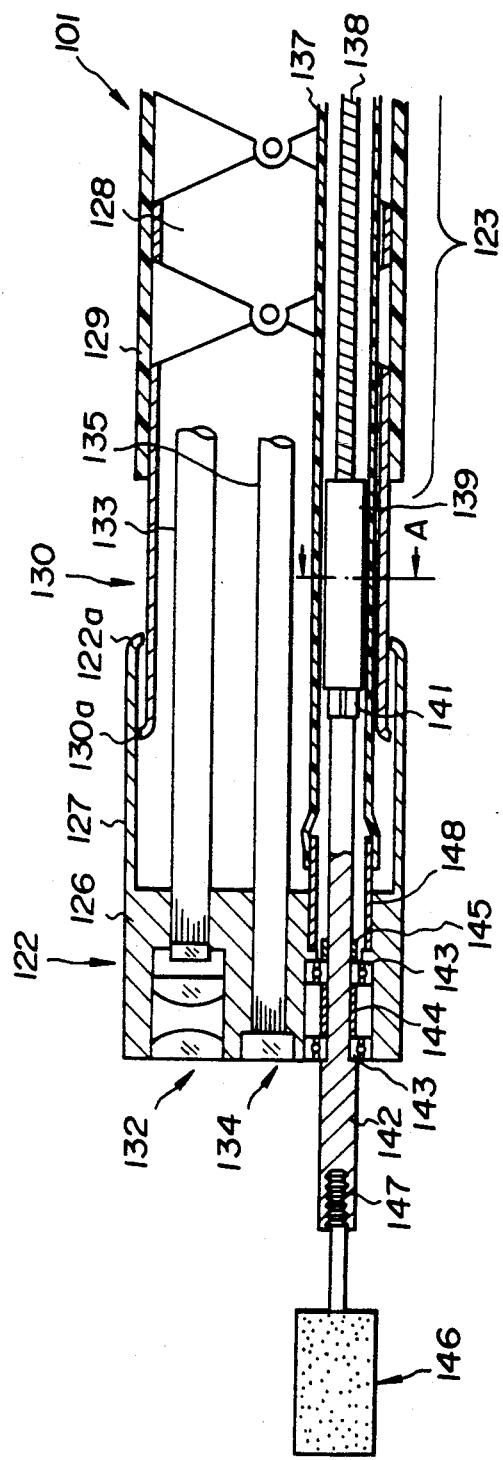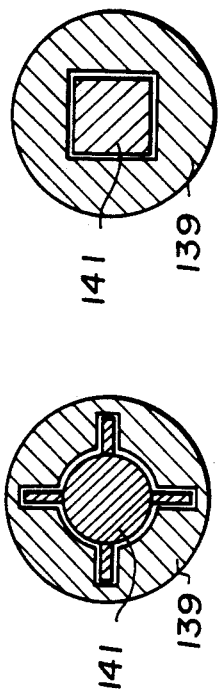

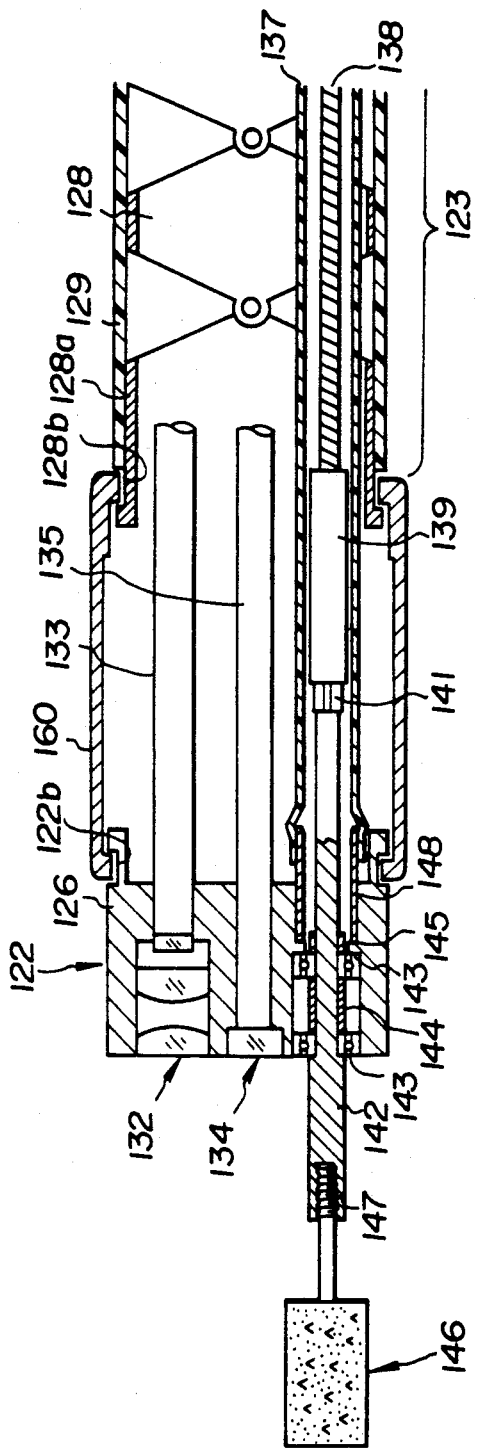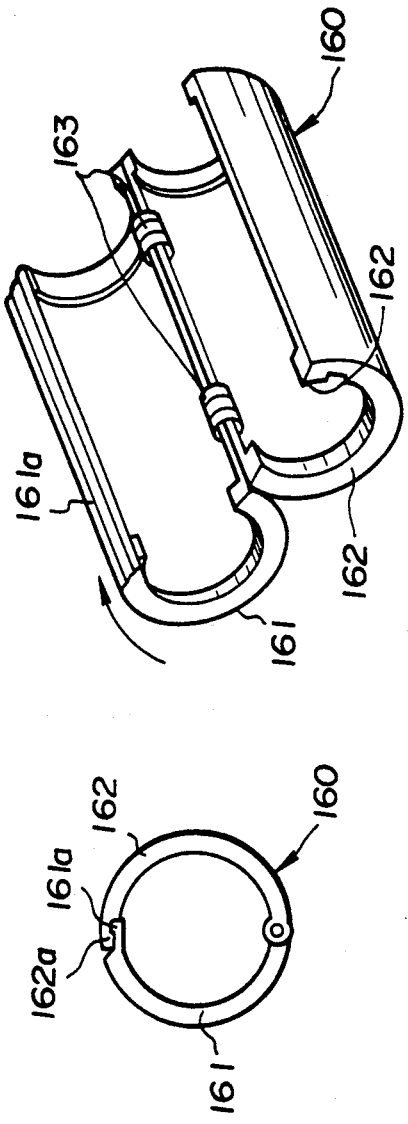

FIG. 31
FIG. 32
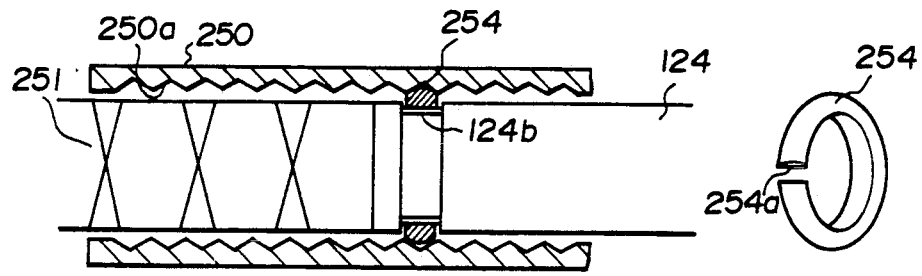
FIG. 33
FIG. 34
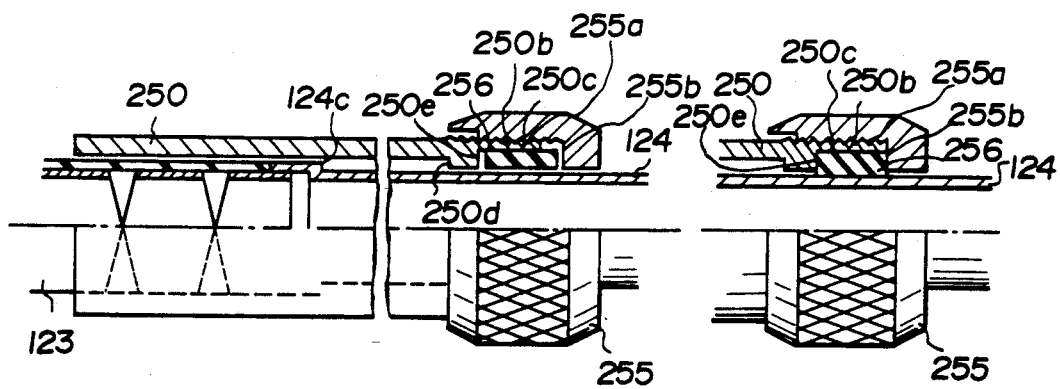

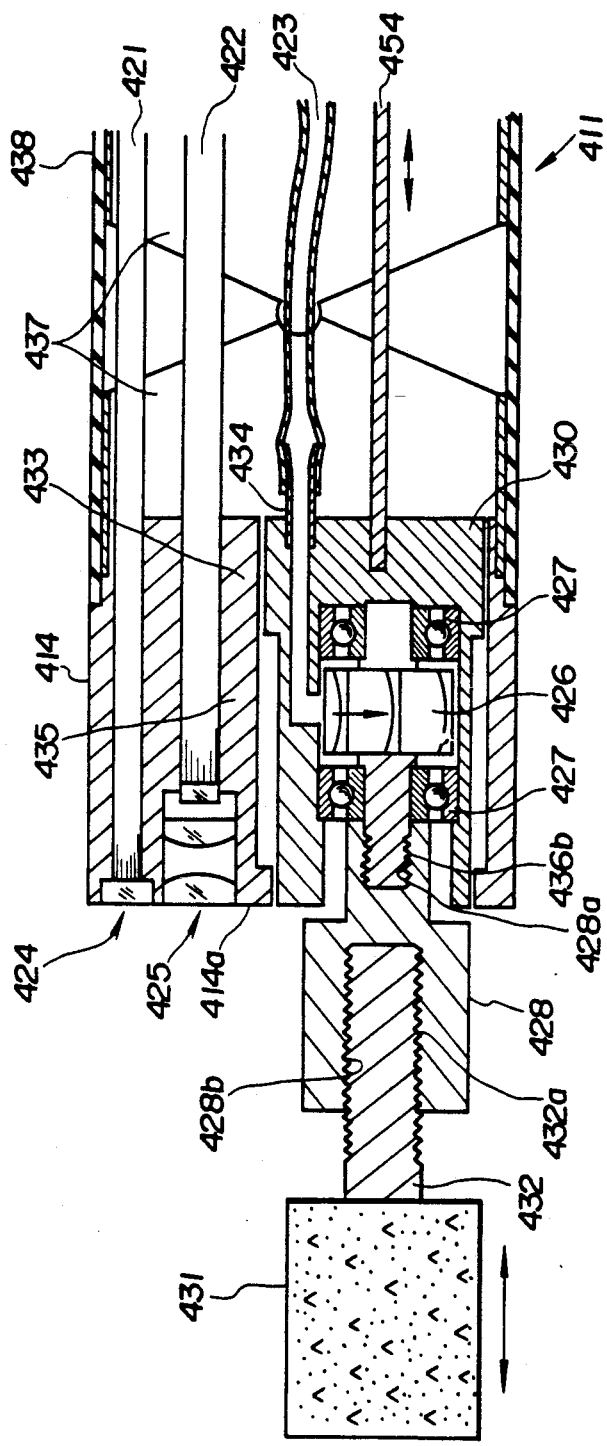
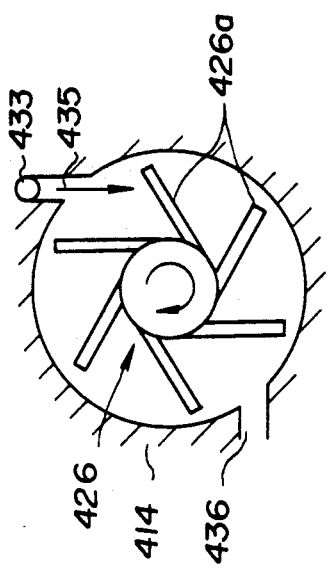
FIG. 39
FIG. 40

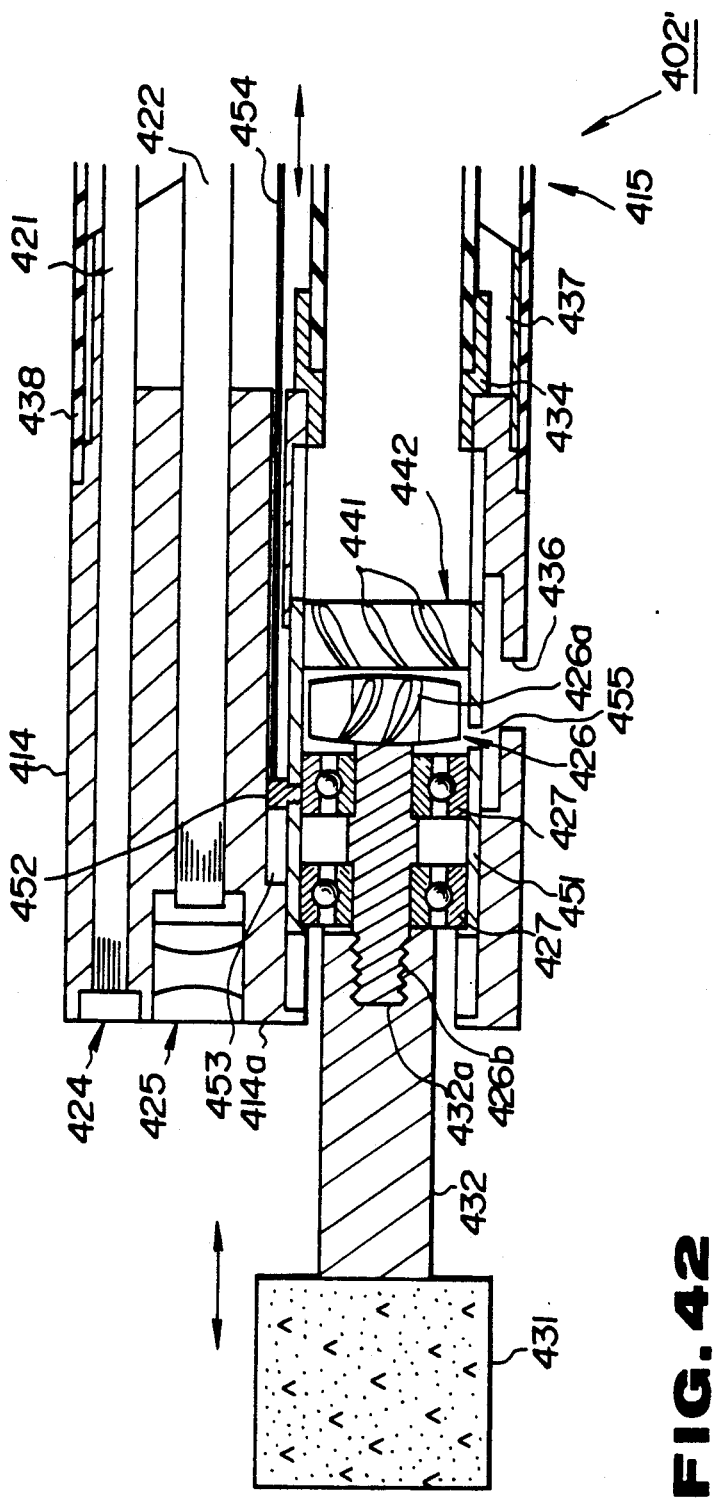

INDUSTRIAL ENDOSCOPE SYSTEM HAVING A ROTARY TREATMENT MEMBER

BACKGROUND OF THE INVENTION AND DESCRIPTION OF THE RELATED ART

The present invention is directed to an industrial endoscope system including a means for moving a rotary treatment member attached to the top end of an endoscope in the axial directions.

In recent years, there has widely been employed an industrial endoscope capable of non-destructively inspecting a chemical plant or an interior of an engine in an industrial field.

Take a jet engine for example, the edge of a turbine blade rotationally driven is damaged in some cases.

In this case, if the damaged portion, though small, is left as it is, the stress concentrates on this damaged portion. The damaged portion is expanded, resultantly. The blade as a whole is required to be replaced.

A countermeasure in the prior arts is such that even if the replacement is not needed, and when a damage is detected, the peripheral portion inclusive of the damaged portion is ground after decomposing the engine.

This method causes a defect in which repairing needs much time.

To cope with this, for instance, Japanese Patent Laid-Open Publication NO. 162924/1983 gives a conventional example. In this example, the top end of an endoscope is fitted with a rotary whetstone for grinding a damaged portion without decomposing the engine.

In the conventional example given above, the rotary whetstone is detachably fitted to the top end of the endoscope for its replacement. Once the whetstone is fitted thereto, the whetstone can not move in the axial directions of the insertion unit, and it follows that treatable portions of the blades are limited. Therefore, some of the blades were not allowed to undergo the treatment by the single endoscope.

Besides, an outside diameter of an insertion portion (access port) for inserting the endoscope into the jet engine is small. In the prior art example described above, the whetstone does not protrude outwards in the radial direction from the outside diameter of the top part of the endoscope. Hence, there exists such a constraint that the whetstones having an extremely small outside diameter are usable. This in turn presents a defect of requiring much time for a grinding treatment.

When grinding a desired part with a whetstone having a different shaft-length, a distance from an objective optical system to a body varies, correspondingly. A defect is arises, wherein conditions for observation also certainly change in the whetstone having the different shaft-length.

BRIEF SUMMARY OF THE INVENTION

It is a primary object of this invention to provide an industrial endoscope system capable of setting the rotary treatment member for grinding in a position suitable for grinding or observation.

It is another object of the present invention to provide an industrial endoscope system capable of facilitating lead-in of a rotary treatment member to a position of a target to be ground.

According to the present invention, a hard top part is formed at the top end of an insertion unit of an industrial endoscope. A rotary treatment member for grinding the target by rotationally driving the treatment member itself is protrusively fitted to the hard top part. The endoscope system also includes a moving means for making at least a distal end of the rotary treatment member movable in the axial directions of the insertion unit. The rotary treatment member can be set in a protrusive position suitable for grinding or observing the target. It is also possible to facilitate the operation of leading the industrial endoscope fitted with the rotary treatment member from an access port.

BRIEF DESCRIPTION OF THE DRAWINGS

Other objects and advantages of the present invention will become apparent during the following discussion taken in conjunction with the accompanying drawings, in which:

FIG. 1 is a block diagram illustrating a whole construction of the first embodiment;

FIG. 2 is a sectional view depicting a top part of an endoscope in the first embodiment;

FIG. 3 is a block diagram showing a construction of a camera control unit;

FIG. 4 is a sectional view depicting a structure of an extrusion quantity adjusting member;

FIG. 5 is a front elevation showing the top part of the endoscope;

FIG. 6 is a side view showing a structure of a rotary driving unit;

FIGS. 7 and 8 are views of assistance in explaining a situation in which a rotary treatment member and the top end of the insertion unit pass through an access port;

FIG. 9 is a view showing a situation to grind a blade;

FIG. 12 is a view illustrating an entire endoscope system in the third embodiment;

FIG. 13 is a sectional view showing a structure of the extrusion quantity adjusting member;

FIG. 15 is a view of a whole endoscope system, illustrating a variant form example;

FIG. 16 is a sectional view depicting the top end of the insertion unit;

FIG. 17 is a view showing a whole endoscope system;

FIG. 18 is a sectional view illustrating a structure of the top end of the insertion unit;

FIG. 19 is a sectional view depicting a structure of the rotary driving unit in a fourth embodiment of the invention;

FIGS. 20 through 23 show a fifth embodiment of the invention;

FIG. 20 is a view showing a whole endoscope system in the fifth embodiment;

FIG. 21 is a sectional view showing the top end of the insertion unit;

FIGS. 22 and 23 are sectional views each showing a slide member;

FIGS. 24 to 26 shown a sixth embodiment of the invention;

FIG. 24 is a sectional view depicting a structure of the top end of the insertion unit in the sixth embodiment;

FIG. 25 is a front elevation showing a holding member;

FIG. 26 is a perspective view of the holding member;

FIG. 27 is a sectional view illustrating the top end of the insertion unit;

FIG. 28 is a view showing a state where the insertion unit is inserted into a jet engine;

FIG. 29 is an explanatory view depicting a state where the insertion unit is inserted into the jet engine;

FIG. 30 is a sectional view illustrating the rear end of a bending part;

FIGS. 31 and 32 shown an example of variant form of the eighth embodiment;

FIG. 31 is a sectional view illustrating the rear end of the bending part;

FIG. 32 is a perspective view showing a C-shaped ring used in the bending part of FIG. 31;

FIGS. 33 and 34 are sectional views each showing the rear end of the bending part in another example of variant form of the eighth embodiment;

FIG. 35 is a view illustrating an entire endoscope system in the ninth embodiment;

FIG. 36 is a vertical sectional view depicting the bending part;

FIG. 37 is a sectional view taken substantially along the line B—B of FIG. 36;

FIGS. 38 through 40 show a tenth embodiment of the invention;

FIG. 38 is a view illustrating an entire endoscope system in the tenth embodiment;

FIG. 39 is a sectional view showing the top end of the insertion unit;

FIG. 40 is a sectional view showing a runner of FIG. 39;

FIGS. 41 and 42 show an eleventh embodiment of the invention;

FIG. 41 is a sectional view showing the top end of the insertion unit in the eleventh embodiment; and FIG. 42 is a perspective view showing the runner of FIG. 41.

DETAILED DESCRIPTION OF THE PREFERRED EMBODIMENTS

Figure 1:
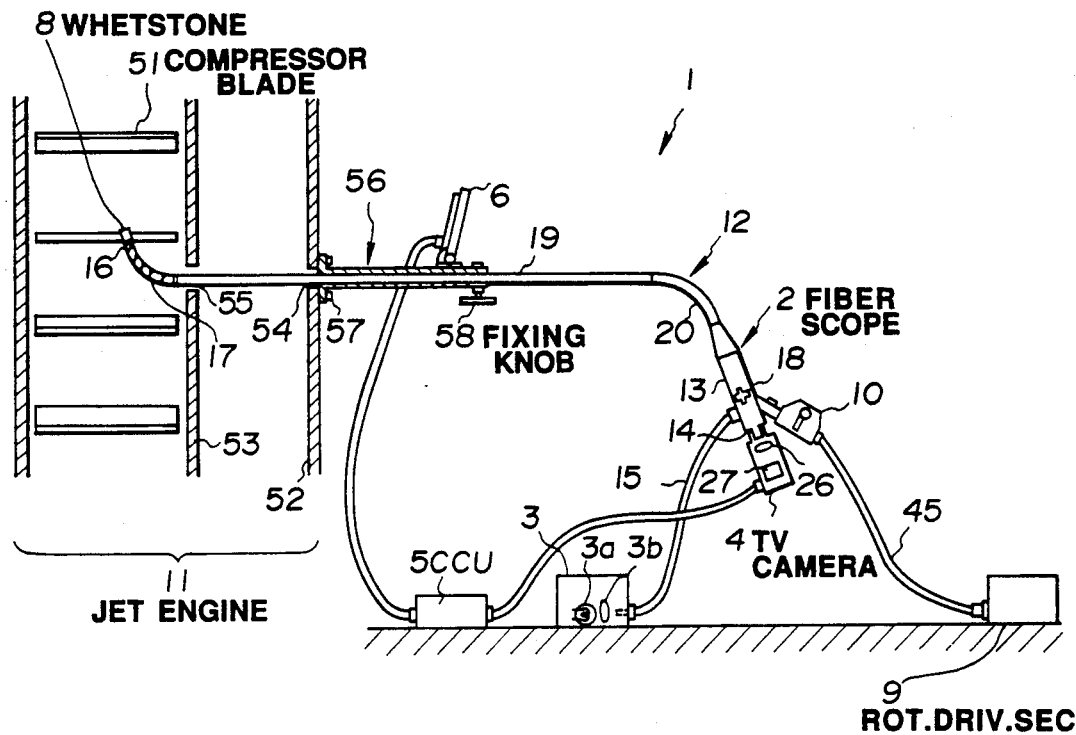
FIGS. 1 through 9 in combination show a first embodiment of the present invention.

An industrial endoscope system 1 is, as depicted in FIG. 1, constructed of a fiber scope 2, a light source apparatus 3, a TV camera 4, a camera control unit (hereinafter abbreviated to CCU), a thin type TV 6, a whetstone 8, a rotary driving section 9 and a protrusion quantity adjusting unit 10. The fiber scope 2 serves as an industrial endoscope. The light source apparatus supplies the fiber scope 2 with illumination light. The TV camera 4 is attached to the fiber scope 2. The CCU 5 processes signals to the TV camera 4. The TV 6 such as a liquid crystal TV displays standard video signals outputted from the CCU 5. The whetstone 8 fitted to the top end of a rotation transmitting member inserted into the fiber scope 2. The rotary driving section 9, to which the rear end of the rotation transmitting member is connected, works to rotationally drive this rotation transmitting member. The adjusting unit 10 is intended to make variable a protrusion quantity of the whetstone protruding from the fiber scope 2.

The fiber scope 2 includes an elongate insertion unit 12 insertable into a subject for inspection such as a jet engine 11 or the like. Formed at the rear end of the insertion unit 12 is a large-diameter operating unit 13. Formed at the rear end of the operating unit 13 is an ocular unit 14 through which a visual observation is effected. A light guide cable 15 extending from the side of the operating unit 13 is connectable to the light source apparatus 3.

The insertion unit 12 is formed as its top end with a hard top part (hereinafter simply referred to as a top part) 16. Behind the top part 16, a bending part 17 is formed adjacently thereto. The bending part 17 is bent vertically or laterally by rotating a bending knob 18 attached to the operating unit 13, thus orienting the top part 16 in desired directions.

An elongate hard part 19 is formed at the rear portion adjacent to the bending part 17. A soft part 20 having an appropriate length is shaped behind the hard part 19, i.e., at the rear end of the insertion unit 12.

A light guide 21 for transmitting the illumination light is inserted into the light guide cable 15 as well as into the insertion unit 12. A connector provided at the end of the light guide cable 15 is connected to the light source apparatus 3. Condensed by a condenser lens 3b are beams of illumination light emerging from a lamp 3a incorporated into the light source apparatus 3. An end face of the light guide 21 is irradiated with the beams of illumination light.

Figure 2:
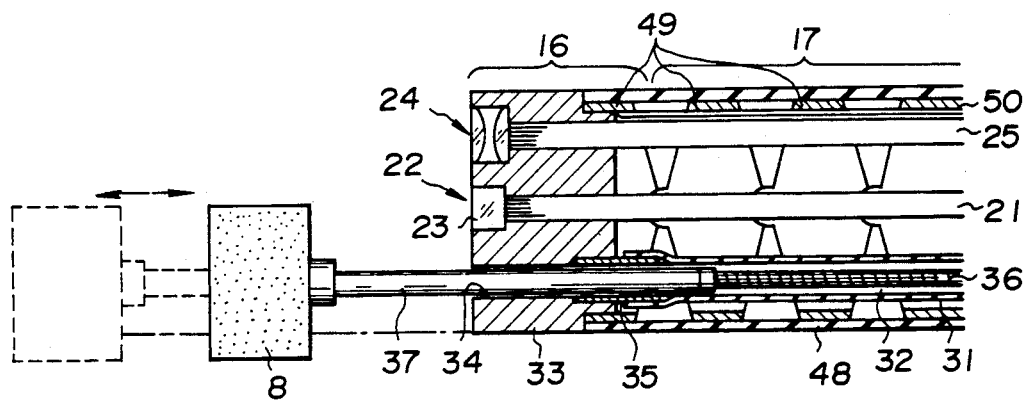

The illumination light falling upon the end face is transmitted via the light guide 21. As illustrated in FIG. 2, the illumination light is emitted forwards via an optical rod (or an optical lens) 23 constituting an illumination optical system 22.

A part to be inspected is illuminated with the illumination light. An optical image of this inspected part is formed on a focal plane of an objective optical system 24 shaped adjacently to the illumination optical system 22. Disposed on this focal plane is one end face of an image guide 25 by which the image is transmitted to the other end face thereof on the side of the ocular unit 14.

Figure 3:
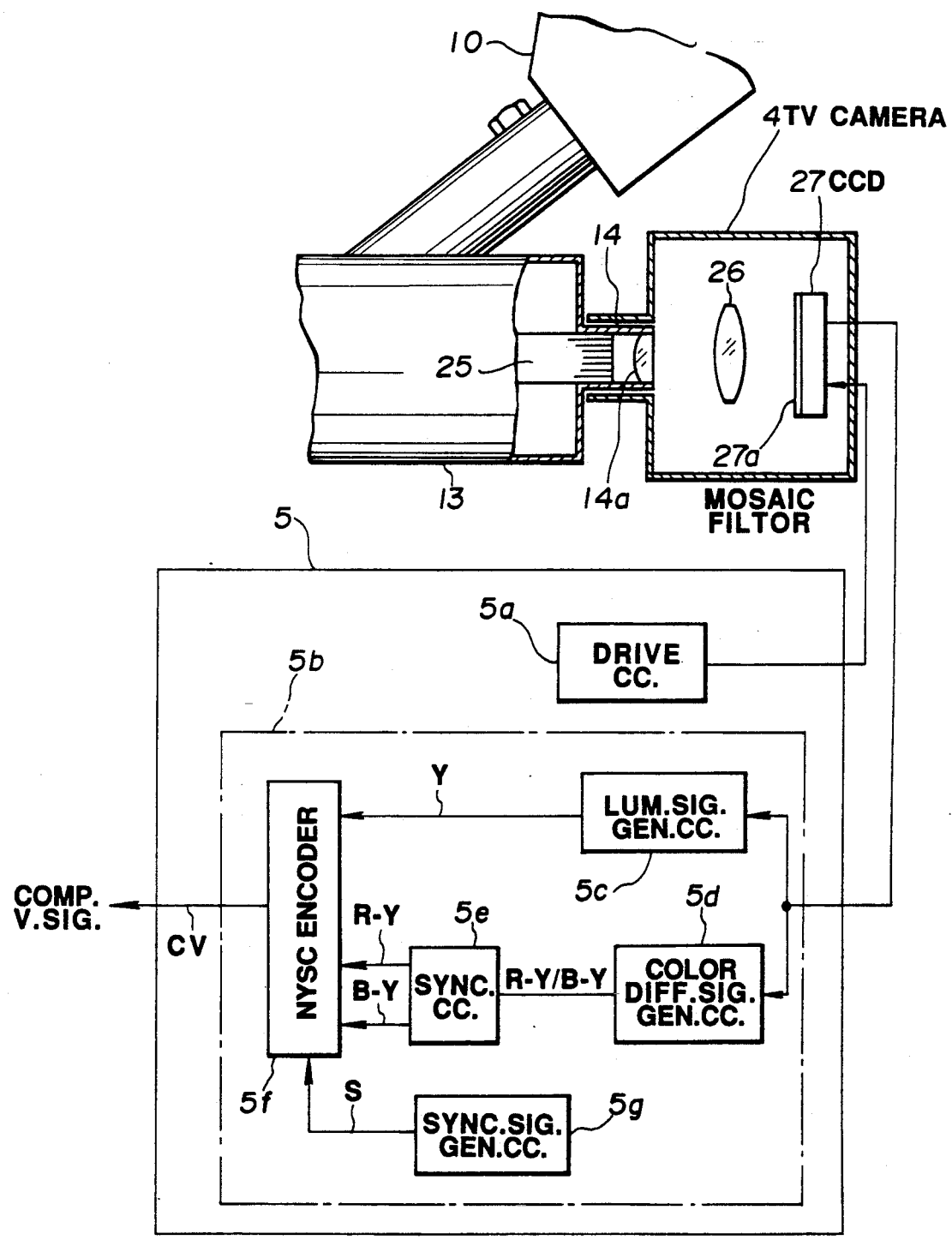

Referring to FIG. 3, the ocular unit 14 includes an ocular lens 14a. The optical image is visually observable via the ocular lens 14a. An image forming lens 26 is incorporated into the externally fitted TV camera 4 detachably attached to the ocular unit 14. The optical image is formed on a CCD 27 serving as a solid state imaging element through the image forming lens 26. A mosaic filter 27a disposed on the front face of the CCD 27 functions to separate colors for every pixel. Video signals which have undergone a photoelectric conversion in the CCD 27 are read by application of drive signals from a drive circuit 5a in the CCU 5. The video signals are then inputted to a luminance signal generating circuit 5c and a color difference signal generating circuit 5d which are combined to constitute a signal processing circuit 5b. The circuits 5c and 5d generate a luminance signal and line sequential color difference signals R-Y/B-Y.

The color difference signals R-Y/B-Y are inputted to a synchronizing circuit 5e, wherein the signals are separated into the synchronized color difference signals R-Y and B-Y. The synchronized color difference signals are inputted together with the luminance signal Y to an NTSC encoder 5f. Synchronizing signals s transmitted from a synchronizing signal generating circuit 5g are overlapped therewith to generate composite video signals CV as standard video signals. The video signals CV are inputted to a thin type TV 6 such as a liquid crystal TV. An optical image formed by the objective optical lens 24 is displayed in color on a TV screen.

A channel 32 is, as depicted in FIG. 2, formed of a soft protection tube 31 inwardly of the insertion unit 12 of the fiber scope 2. The top end of the tube 31 is fixed via a connecting pipe 35 to a through-hole 34 bored in a top end member 33 constituting the top part 16.

The rear end of the channel 32 is open to the operating unit 13. In a first embodiment, however, a flexible shaft 36 is inserted into the channel 32. The whetstone 8 is fixed to a hard connecting shaft 37 fixed to the top end of the flexible shaft 36.

Figure 5:
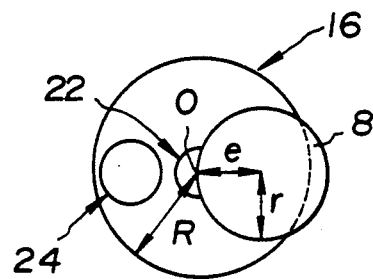

The whetstone 8, as illustrated in FIG. 2 or 5, assumes a cylindrical configuration. As shown in FIG. 5, the whetstone 8 protrudes forwards so that it is decentered with an eccentric quantity e from the center 0 of the top part 16.

The whetstone 8 is disposed so that on the basis of a radius R of the top part 16, a radius r of the whetstone 8 projects outwards in the radial direction from a line of extension of the radius R.

Figure 4:
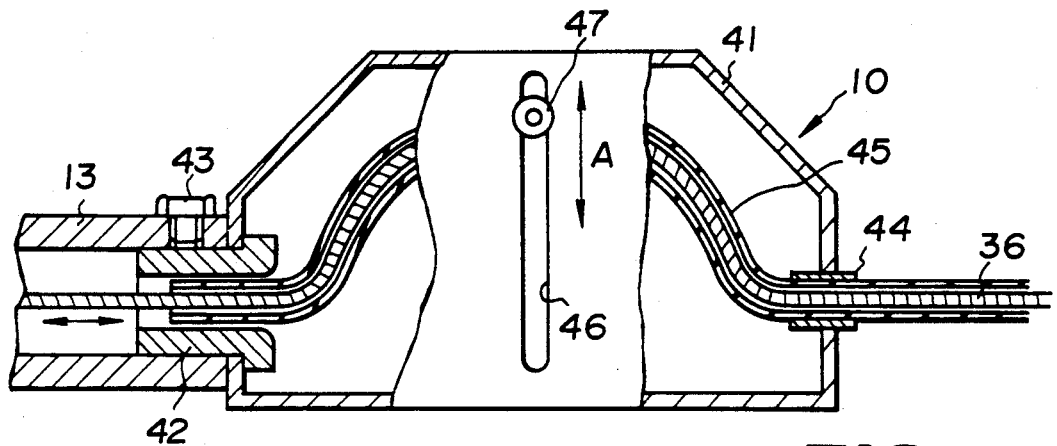

FIG. 4 shows a structure of an extrusion quantity adjusting member 10 fitted in a channel opening of the operating unit 13.

Fitted in the channel opening is a fitting pipe 42 fixed to a case 41 of the extrusion quantity adjusting member 10. The pipe 42 can be detachably fixed with a fixing screw 43 driven from a die portion.

The flexible shaft 36 penetrates the case 41 via a pipe 44 secured in an opening of the case 41 on the opposite side of the pipe 42. The flexible shaft 36 is covered with a soft protection tube 45. The as-covered shaft 36 is pulled out therefrom. The top end of the flexible shaft 36 is connected to the rotary driving section 9. Note that the protection tube 45 is fixed to the pipe 44.

The case 41 accommodates the flexible shaft 36 passing through the soft protection tube 45 in such a way that the shaft 36 is bendable in, e.g., a semi-circular shape. Fixed to the protection tube 45 in the case 41 is a proximal end of an extrusion quantity adjusting knob 47 projecting from a slot 46 bored in a substantially central portion of the case 41.

However, the knob 47 protruding from the slot 46 is shiftable along the slot 46 in arrowed directions A. With this arrangement, the flexible shaft 36 can be thrust forwards by making variable a bending quantity of the shaft 36; or alternatively the extruded shaft 36 can be moved backwards.

In a state shown in, e.g., FIG. 4, a solid line of FIG. 2 depicts an aspect of the whetstone 8 fitted via the connecting shaft 37 to the front end of the flexible shaft 36. The flexible shaft 36 is thrust forwards by shifting down the knob 47 from the position shown in FIG. 4. At this time, as indicated by a dotted line of FIG. 2, the whetstone 8 can be protruded forwards, i.e., in the axial directions of a rotary shaft. Note that in FIG. 2, the bending part 17 adjacent to the top part 16 is covered with a sheath 48. A multiplicity of bending pieces 49, 49, ... are rotatably connected inwardly of the bending part 17.

One end of a bending operation wire 50 (only one wire is illustrated for simplicity) is fixed to, e.g., the outermost bending piece 49. When pulling this wire 50, the bending part 17 is bent so that the wire-fixed portion is directed inwards.

Note that the (hard) top part 16 extends from the front end of the top end member 33 to the rear end of the outermost bending piece 25.

Figure 6:
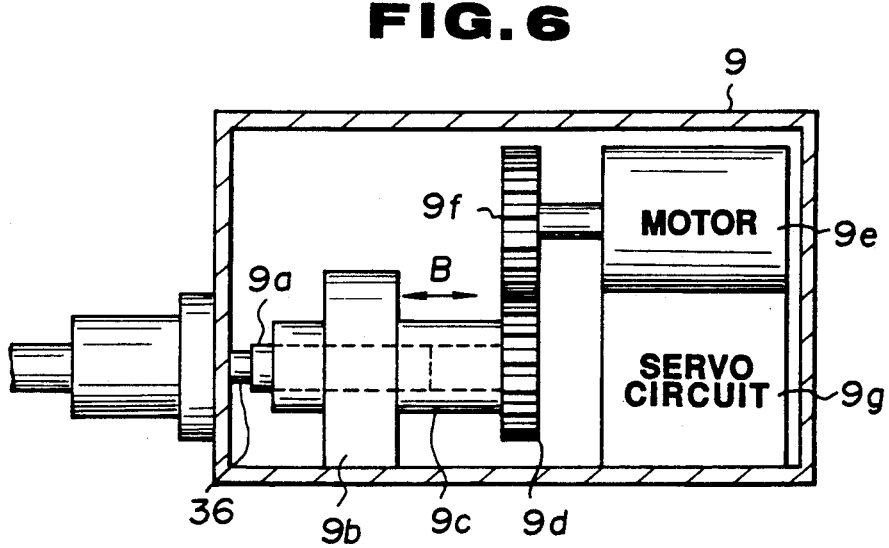

As illustrated in FIG. 6, a slide member 9a assuming a square in section is attached to the end of the flexible shaft 36 encased in the rotary driving section 9. The slide member 9a is fitted into a hole of a shaft receiving member 9c rotatably supported on a bearing 9b. The slide member 9a is slidably movable in the arrowed directions B within the hole. The shaft receiving member 9b is fitted with a gear 9d meshing with a gear 9f rotated by a motor 9e. Rotations of the motor 9e are controlled by a servo circuit 9g. The hole of the shaft receiving member 9c is formed long. The hole is rotationally driven together with the shaft receiving member 9c even when changing an inserting position of the slide member 9a.

In the fiber scope 2, as illustrated in FIG. 1, for instance, when a compressor blade 51 of a jet engine 11 was found to be damaged during an inspection, a grinding process can be effected by use of the whetstone 8.

In the case of grinding, the top end of the insertion unit 12 fitted with the whetstone 8 is led to the blade 51 via access ports 54 and 55 of partition walls 52 and 53 of the jet engine 11. In this case, an insertion unit fixing jig 56 is fixed to the partition wall 52 formed with the access port 54 by use of screws 57. The insertion unit 12 can thus be inserted smoothly.

When inserting the member 12 up to an easy-to-grind position, the hard part 19 is arranged to be fixable with a fixing knob 58. Besides, an easy-to-observe operation can be attained by mounting the thin type TV 6 on the insertion fixing jig 56 or attaching it with magnets or the like.

Figure 7:
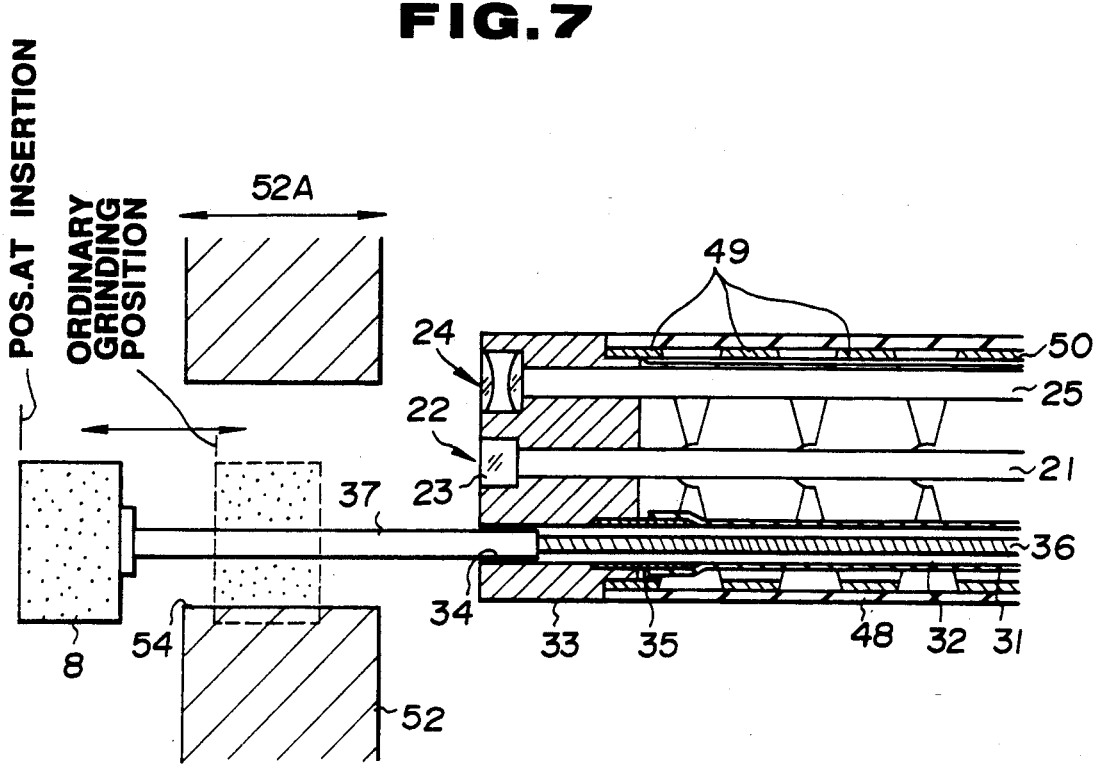
Figure 8:
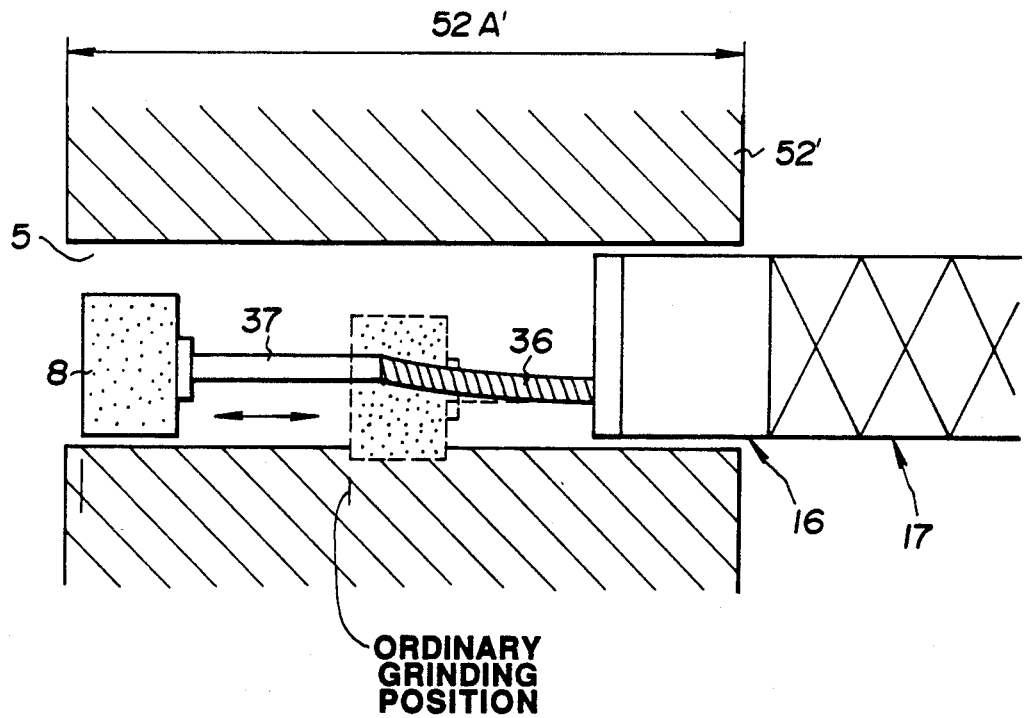

If a diameter of an opening of, e.g., the access port 54 is smaller than the maximum dimension, i.e., (R+e+r) of the top part fitted with the whetstone 8 (of course, D>2R, D>2r), the insertion unit can be inserted in the manner shown in FIG. 7 or 8.

If, as shown in FIG. 7, a thickness 52A of the partition wall 52 is small, the whetstone 8 is protruded so that a spacing between the top end face and the whetstone 8 is larger than the thickness 52A. In this state, after inserting at first the whetstone 8, the top part 16 may pass therethrough by moving it in the direction opposite (downwards in FIG. 7) to the eccentric direction of the whetstone 8. Incidentally, the dotted line indicates a state where the whetstone 8 is in an ordinary grinding position. This implies that the access port 54 does not admit the whetstone 8, if the whetstone 8 is forced to be inserted while being set in this state. Namely, when being fixed in the ordinary grinding position as in the conventional example, a large whetstone 8 can not be fitted. As in the first embodiment, however, the whetstone 8 is protrusively shifted towards the rotary shaft thereof, the access portion 54 having a small diameter D permits the passage. In this case, the passage is permitted even when all of the hard connecting pipe 37 is not protruded.

If, as illustrated in FIG. 8, a thickness 52A' of, e.g., a partition wall 52' is larger, at least the whole hard connecting pipe 37 is protruded forwards from the top part, and the flexible shaft 36 is arranged to be bendable.

Because of the flexible shaft 36 being bent, even when the eccentrically attached whetstone 8 projects outwards from an outside diameter 2R of the top part 16 in the radial direction, the passage is permitted.

Note that in FIG. 8, the dotted line shows the ordinary grinding position. In this case also, only the whetstone having an outside diameter smaller than the diameter of the top part is allowed for its attachment in the apparatus wherein the axial movement is inhibited as seen in the prior art example. In accordance with the first embodiment, however, there is no such constraint. Hence, a grinding capability can be increased. The grinding process can be finished in a short time.

According to the first embodiment, the protrusion quantity of the whetstone 8 is variable, and hence a degree of freedom goes up. This in turn facilitates the grinding operation.

Figure 9:
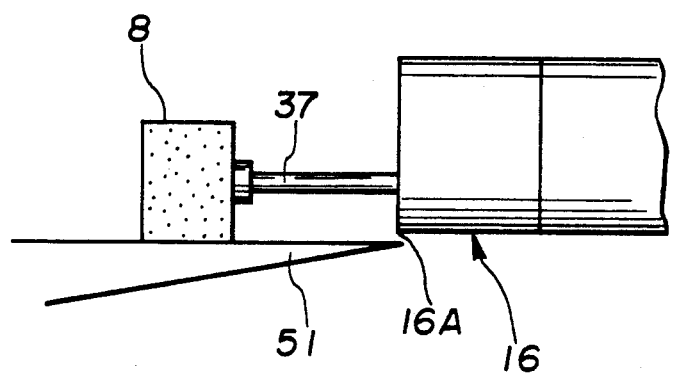

As illustrated in e.g., FIG. 9, when one surface of the blade 51 is ground flat, the arrangement that the whetstone 8 protrudes outwards from the outside diameter of the top part 16 in the radial direction reduces more of difficulty of grinding due to contact of the whetstone 8 with an outer peripheral portion 16A of the top part. When grinding the blade disposed more forwards than the position shown in FIG. 9, the front end of the top part impinges on the top end of the blade 51. It is because the protrusion quantity is invariable in the conventional example. This makes the grinding operation difficult. In contrast with this, the grinding operation can be carried out without causing such inconvenience in accordance with the first embodiment.

As discussed above, the first embodiment exhibits many advantages in which the grinding capability is improved, grinding is easier than in the prior art example, and the small access port admits the passage even when fitting the whetstone 8 having large dimensions.

After passing through the access port, when grinding a portion to be ground, as illustrated in FIGS. 7 to 9, grinding is performed by setting the whetstone 8 in an ordinary grinding position (suitable for the whetstone that is on the grinding process or observing the portion to be ground). That is, grinding can be effected by making constant a distance to the subject. Besides, in such a special working state as to use only angular parts of the whetstone 8, grinding can be performed by setting the whetstone 8 in a protrudent position suited to this grinding process.

It is to be noted that a whetstones 8 having different dimensions is also usable for replacement. In this case, the whetstone 8 may be replaced together with the connecting pipe 37 and the flexible shaft 36. Furthermore, the whetstone 8 is detachably fitted to the connecting pipe 37, and only the whetstone 8 may be replaced corresponding to the processes such as grinding and the like.

Figure 10:
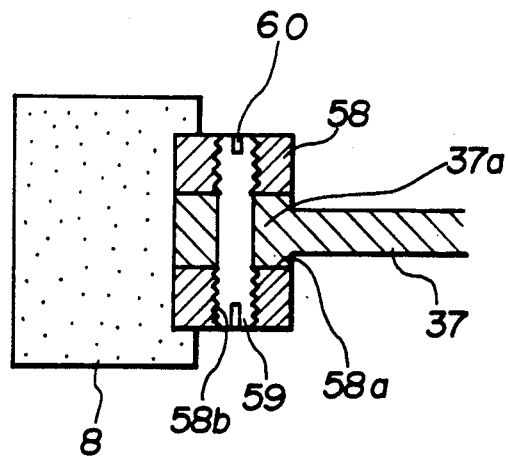
FIG. 10 is a sectional view showing a mechanism for attaching or detaching the rotary treatment member.

FIG. 10 shows one structural example where the whetstone 8 is detachably fitted to the connecting pipe 37. A pipe sleeve receiving member 58 attached to the central portion of the rear face of the whetstone 8 is formed with, e.g., a square hole 58. A square pipe sleeve 37a of the flexible shaft 37 can be fitted into the square hole 58a. The pipe sleeve receiving member 58 is also formed with a screw hole 58b extending across the hole 58a. A screw 59 is screwed passing through a hole bored in the pipe sleeve 37a fitted into the hole 58a. The whetstone 8 is thus detachably fitted to the flexible shaft 37. Incidentally, protrusions (protruding inwards in the radial direction) at both ends of a C-shaped ring 60 are fitted into bores formed at both ends of the screw 59, thus preventing come-off of the screw 59.

Figure 11:
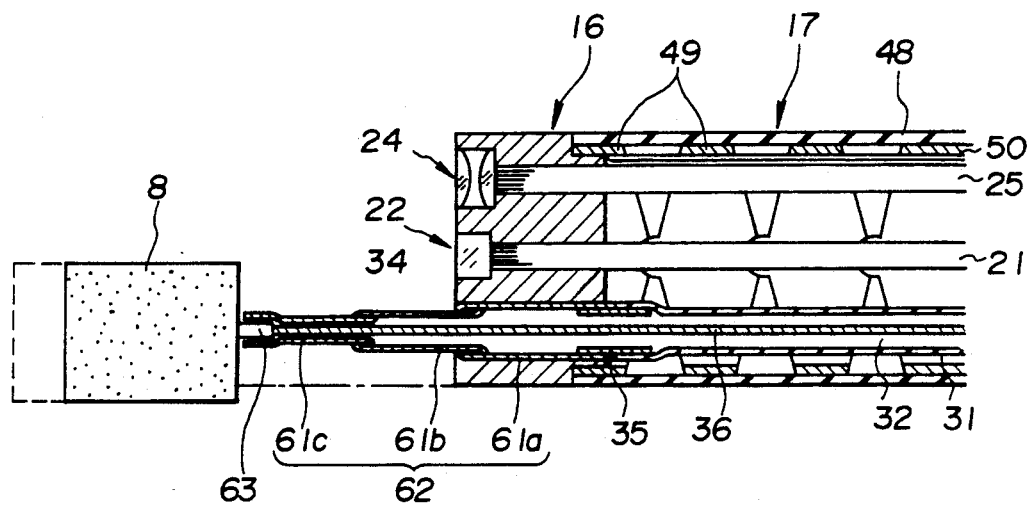
FIG. 11 is a sectional view illustrating the top end of the insertion unit in a second embodiment of the invention.

Turning to FIG. 11, there is illustrated principal portions of a second embodiment of this invention.

Fixedly fitted in a through-hole 34 of the top part 16 in accordance with the second embodiment is a connecting pipe 62 consisting of a plurality of hard sub-pipes 61a, 61b, ... which are, as in the way with a rod antenna, slidable on each other. The flexible shaft 36 is inserted into the connecting pipe 62. The top end of the flexible shaft 36 is fitted with the whetstone 8 through a fixing ring 63.

Note that a connecting pipe 35 is fixed to the rear end of the hard sub-pipe 61a fixedly fitted in the through-hole 34, and the top end of the protection tube 31 is fixed to the pipe 35.

Other components are constructed in much the same way as that of the first embodiment.

In this second embodiment, a protrusion quantity of the flexible shaft 36 is changed on this side of the shaft 36. A length of an extension pipe 62 is made variable by slidably shifting the hard sub-pipe 61b with respect to the sub-pipe 61a, the sub-pipe 61c with respect to the sub-pipe 61b and so on. With this arrangement, the whetstone 8c can be set in an arbitrary position in front of the top part 16.

In the second embodiment, the extension pipe 62 is variable in length. If a variable length quantity is set larger than a thickness of the partition wall, a function similar to that of the first embodiment can be exhibited.

Figure 12:
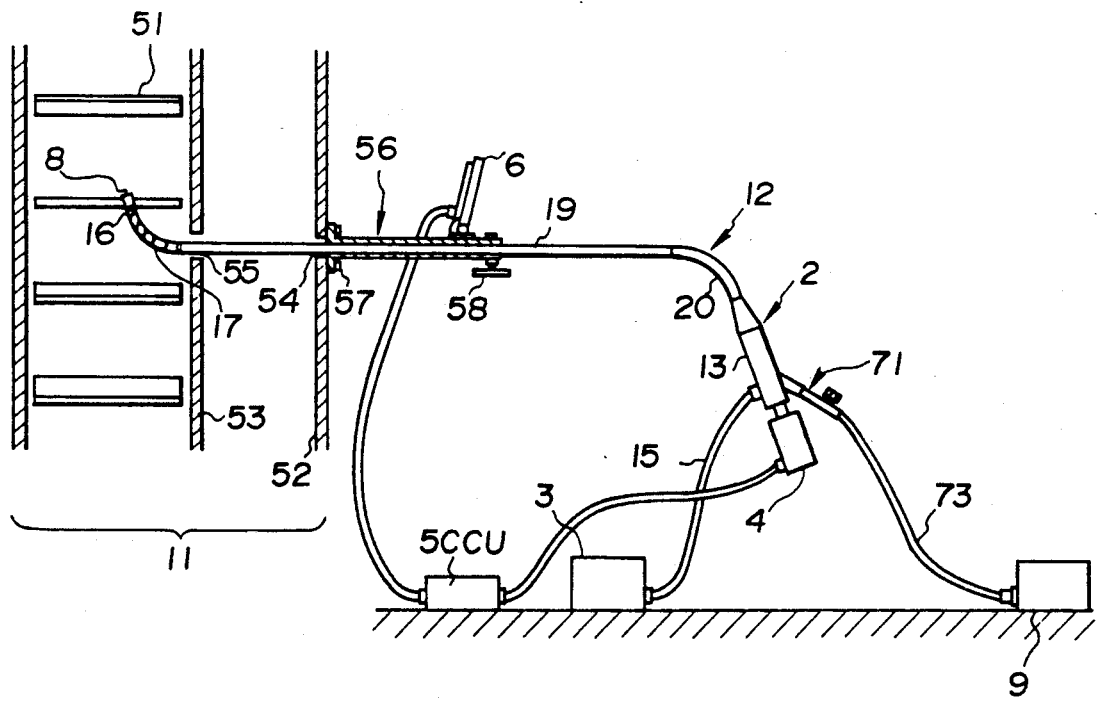
FIGS. 12 to 14 in combination show a third embodiment of the invention.

A third embodiment demonstrated by FIG. 12 employs an extrusion quantity adjusting member 71 different from the extrusion quantity adjusting member 10 used in the first embodiment.

Figure 13:
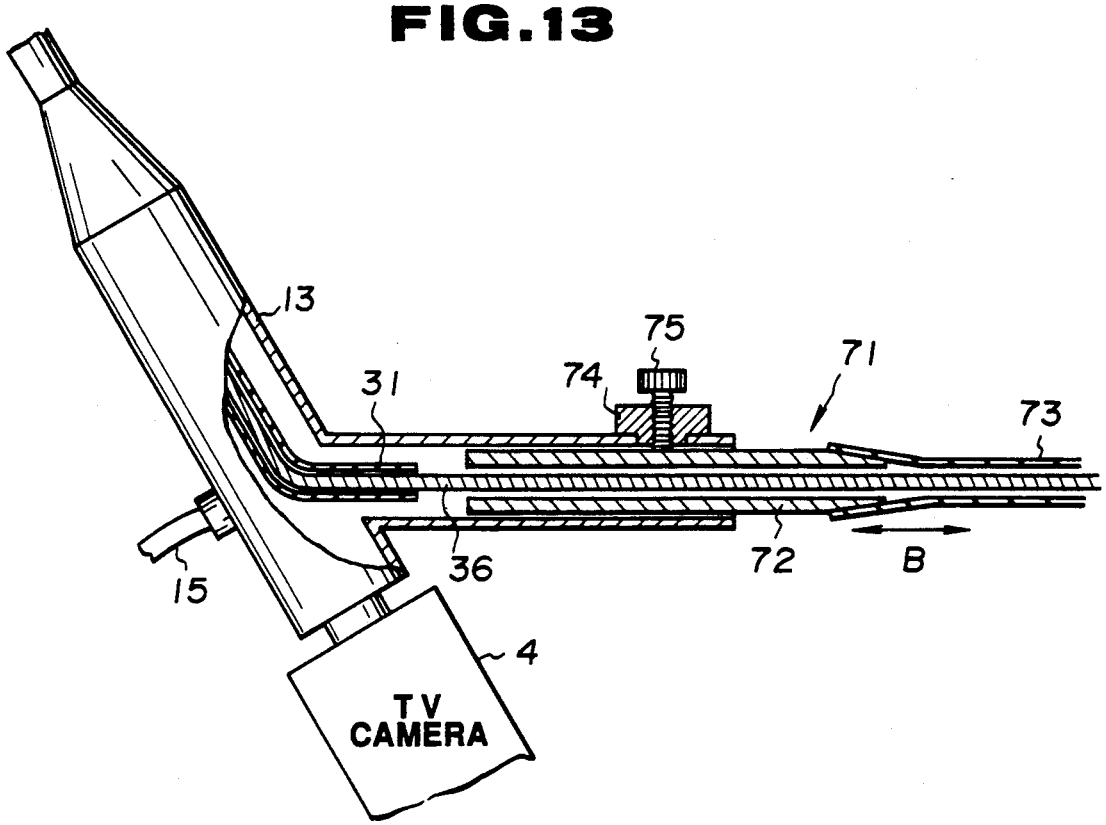

As depicted in FIG. 13, the flexible shaft 36 inserted through the operating unit 13 is exposed from the protection tube 31 in the vicinity of a channel opening. The shaft 36 is further inserted through a movable slide connecting member 72 at the channel opening. The front end of a protection cord 73 is fixed to the tapered rear end of the slide connecting member 72.

Supporting nut 74 is fixedly fitted in a lateral bore of the opening. A bolt 75 for fixing the supporting nut 74 is screwed therein. The fixing bolt 75 is gyrated enough to protrude its top end, thereby stopping the shift of the slide connecting member 72. The fixing bolt 75 is slackened, whereby the slide connecting member 73 is shiftable in the arrowed directions B. With this shifting, the whetstone 8 can be protruded to an arbitrary length from the top part 16.

Figure 14A:
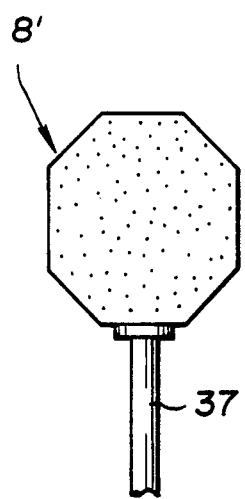
FIGS. 14a and b are side views illustrating configurations of whetstones.
Figure 14B:
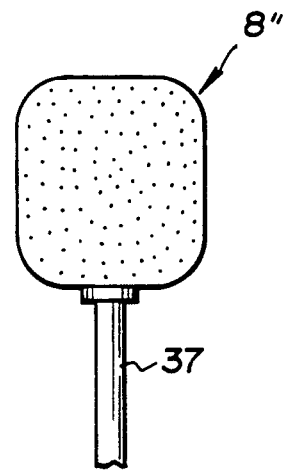

In the third embodiment, as shown in FIG. 14a or 14b, there is employed a whetstone 8' whose angular portions are chamfered or a whetstone 8" the angular portions of which are rounded to facilitate both insertion and removal.

Other components are constructed in the same manner as that of the first embodiment. The same members are marked with the like symbols, and the description thereof is omitted.

The functions and effects in the third embodiment are substantially the same as those of the first embodiment.

Figure 15:
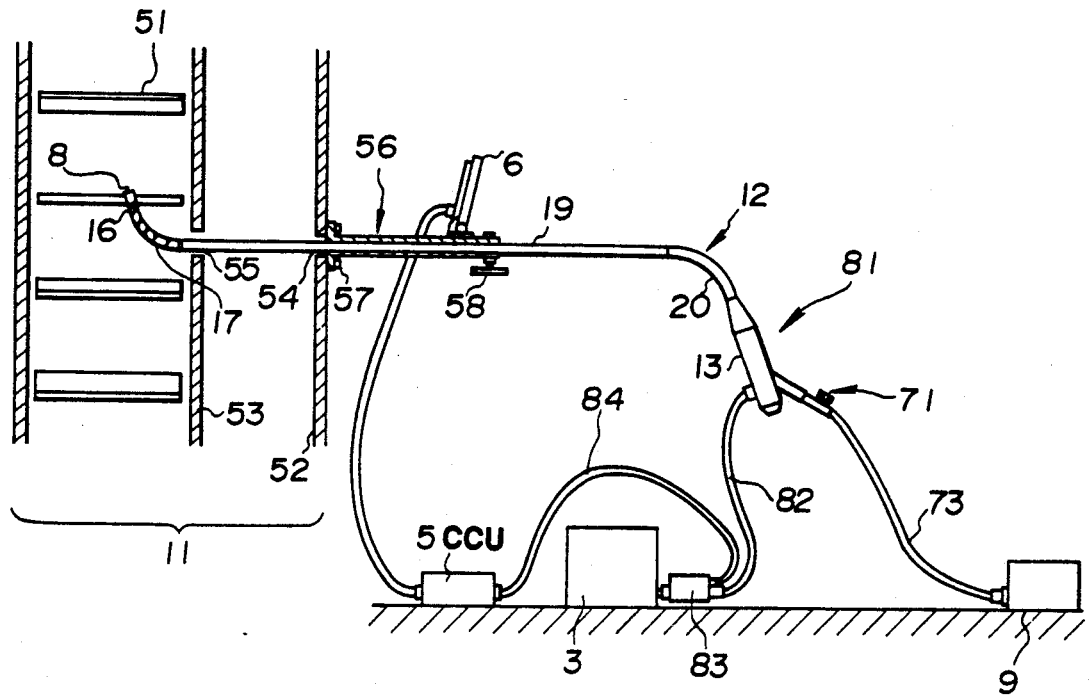
FIGS. 15 and 16 show an example of variant form of the third embodiment.

FIG. 15 shows an entire variant form of the third embodiment of this invention.

In an example of this variant form, a video scope (electronic scope) 81 is employed in place of the fiber scope 2 and the TV camera 4 mounted on this fiber scope 2.

Figure 16:
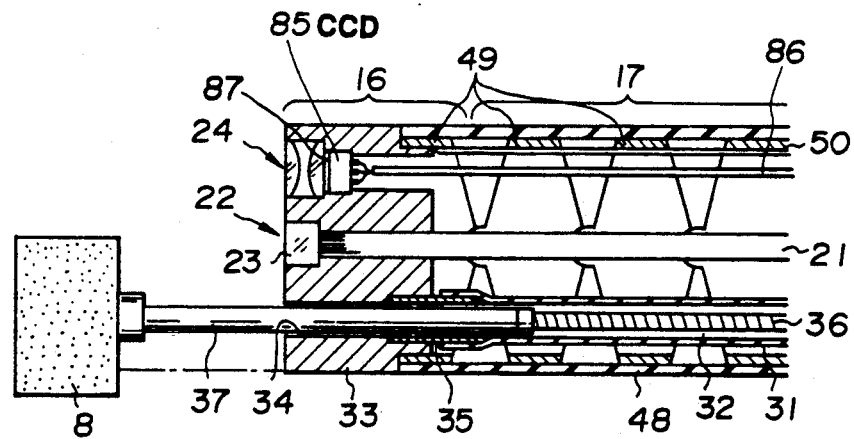

The video scope 81 includes the fiber scope 2, the insertion unit 12 and the operating unit 13 which are all the same as those in the third embodiment. A universal cord instead of the light guide cable 15 extends from the operating unit 13. A connector 83 at the top end of the universal cord 82 is connected to the light source apparatus 3, thereby supplying the illumination light. A signal cable 84 extending from the connector 83 is connected to the CCU 5, whereby the signals to the video scope 81 can be processed. As illustrated in FIG. 16, a CCD 85 is disposed on a focal plane of an objective lens 24. A signal line 86 is connected to individual leads projecting from the rear face of the CCD 85. The signal line 86 extending from the operating unit 13 is inserted through the universal cord 82. The line 86 also passes through the signal cable 84 and is connected to the CCU 5. Note that a mosaic filter 87 is disposed in front of a light receiving plane (photoelectric converting plane) of the CCD 85.

Other components are the same as those of the third embodiment. The same components are marked with the like symbols, and the description thereof is omitted.

Figure 17:
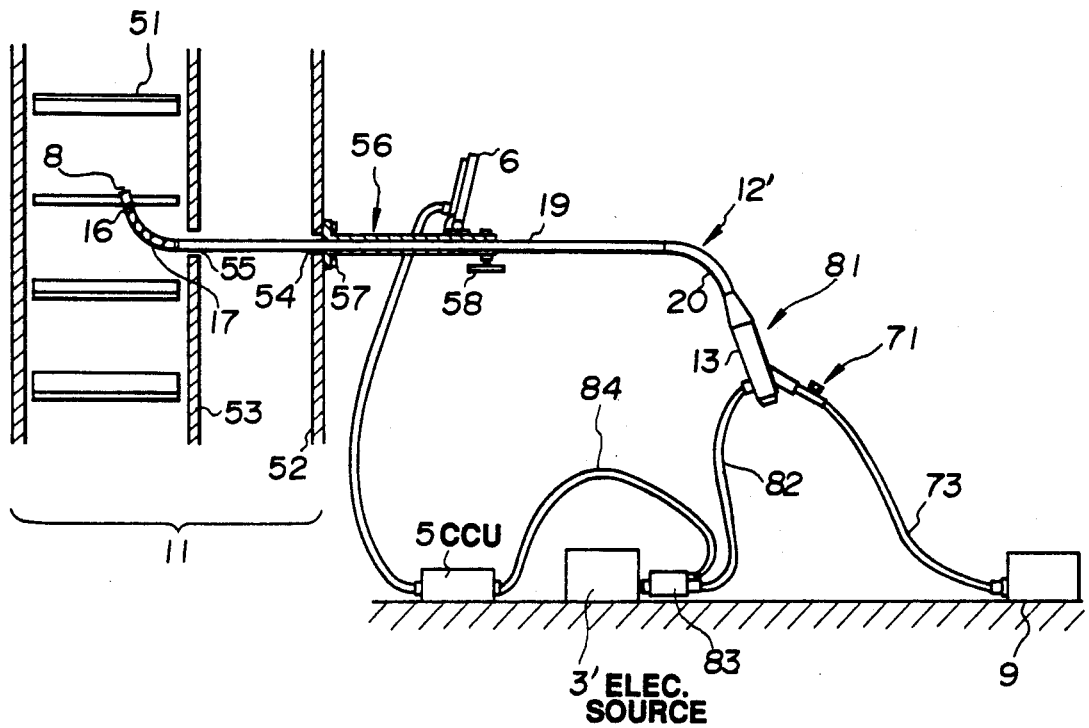
FIGS. 17 and 18 show another example of variant form of the third embodiment.
Figure 18:
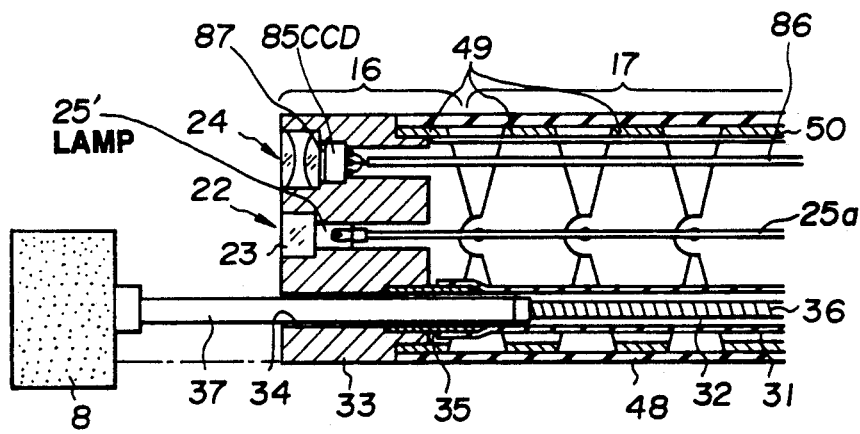

FIG. 17 shows an example of variant form of the fourth embodiment. In this variant form example, there are used an electric source apparatus 3' as a substitute for the light source apparatus 3 and also a video scope 12' having no light guide 25. Referring to FIG. 18, an illuminating lamp 25' is provided at an inner portion of the illumination optical system 22 within the top part 16. The illuminating lamp 25' becomes luminescent with electric power supplied via the signal line 25a from the electric source apparatus 3'. The lamp 25' emits the illumination light through the illumination optical system 22.

Other components have the same constructions as those of the fourth embodiment. The same components are marked with the like symbols, and the description thereof is omitted.

The functions and effects of this variant form are the same as those of the fourth embodiment.

FIG. 19 illustrates the principal portions in the fourth embodiment of the present invention.

In the fourth embodiment, a rotary driving section 91 is mounted in an opening of the operating unit 13.

The rotary driving section 91 accommodates a motor 92 fixed via a motor fixing member 93 to a motor base 94 fitted with a rack 95. A pinion 96 engaging with the rack 95 is rotated, whereby the motor 92 is movable together with the rack 95 in the arrowed directions C. Note that a guide 99 is provided on the opposite side to the rack 95. A rotary shaft of the pinion 96 is fitted with an extrusion quantity adjusting dial 97. A flexible shaft 36 is extruded or retracted by rotating the dial 97, thus variably setting the whetstone 8 protruding from the top part in an arbitrary protrusive position.

It should be noted that a cable 98 connected to the motor 92 is connected to an electric source. The motor 92 is turned ON/OFF by use of, e.g., an unillustrated fit switch or an unillustrated switch provided in an appropriate position on the outer periphery of the rotary driving section 91.

Other components are the same as those of the third embodiment. The same members are marked with the like symbols.

The functions and effects of the fourth embodiment are almost the same as those of the first embodiment.

The respective embodiments discussed above each have such a structure that the rotary treatment member is movable in the axial directions of the insertion unit of the endoscope. The top part, the bending part and the hard part of the insertion unit are all not movably constructed.

Whereas in an embodiment which will hereinafter be described, the top end (hard part) of the endoscope is movable together with the rotary treatment member in the axial directions of the insertion unit.

An industrial endoscope system 100 in a fifth embodiment is, as depicted in FIG. 20, composed of an endoscope 101, a light source apparatus 102 connected to the endoscope 101, a rotary driving section 103 and a controller 105, connected to the rotary driving section 103, for controlling the number of rotations.

A fit switch 107 is connected via a cable 106 to the controller 105.

The endoscope 101 includes an elongate insertion unit 108 and an operating unit 109 formed in continuation from the rear end of the insertion unit. The endoscope 101 also includes a light guide cable extending sideways from the operating unit 109. A connector 111 detachably connected to the light source apparatus 102 is provided at the end of the light guide cable 110. A connecting member 112 is disposed at the rear end of the operating unit 109. The operating unit 109 is connected via this connecting member 112 to a rotary driving section 103.

An ocular unit 113 is so attached to the connecting member 112 as to be orthogonal to the axial directions thereof. A TV camera 115 is installed through an adaptor 114 at the rear end of the ocular unit 113.

The TV camera 115 is linked via a cable 116 to a CCU 117. The signals are processed by the CCU 117 and then displayed on a monitor 118.

The insertion unit 108 comprises, sequentially from its top end, a top part 122, a bendable bending part 123 and a hard part 124. The bending part 123 is bendable in the up-and-down/right-and-left directions by manipulating a bending knob 125 attached to the operating unit 109. As illustrated in FIG. 21, the top part 122 has a top part body 126 assuming a cylindrical shape. A cylinder 127 is disposed in rear of the top part body 126. A projection 122a projecting inwards is provided at the rear end of the cylinder 127. The bending part 123 has a plurality of ring-like bending pieces 128 rotatably liked to each other. A sheath 129 covers the outer peripheries of bending pieces 128. A cylindrical member 130 is provided at the front end of the bending part 123. A projection 130a projecting outwards is formed at the front end of the cylindrical member 130. The cylindrical member 130 is fitted into an interior of the cylinder 127 of the top part body 126. With this arrangement, the top part body 126 is slidable along the cylindrical member 130 in the axial directions. The projections 122a and 130a are shaped to press both the outer periphery of the cylindrical member 130 and the inner periphery of the cylinder 127. The projections 122a and 130 cooperate to prevent a removal of the top part body 126.

A top end face of the top part body 126 is formed with an observation window, an illumination window and an opening for a treatment member. An objective optical system 132 is provided inwardly of the observation window. A top end face of an image guide 133 is disposed in an image-forming position of the objective optical system 132. The image guide 133 is inserted into the insertion unit 108 and also the operating unit 109. A rear end face of the image guide 133 confronts an unillustrated ocular lens incorporated into the ocular unit 113. A subject image formed by the objective optical system 132 is transmitted via the image guide 133 to the ocular unit 113. The image can be observed through this ocular unit 113. An illumination optical system 134 is provided in an interior of the illumination window. A light guide 135 is provided in continuation from the rear end of the illumination optical system 134. The light guide 135 is inserted into the insertion unit 108, the operating unit 109 and a light guide cable 110 as well. An incident end is connected to a connector 111. The illumination light emerging from a light source apparatus 102 is made incident upon the incident end.

Inserted into the insertion unit 108 is a flexible rotary force transmitting member 138 covered with a protection tube. An outer slide member 139 is connected to the front end of the rotary force transmitting member 138. Connected to the rear end of the rotary force transmitting member 138 is an output shaft of an unillustrated motor disposed within the rotary driving section 103 connected via the connecting member 112 to the operating unit 109. The outer slide member 139 is connected to an inner slide member 141. The outer/inner slide members 139 and 141 are slidable in the axial directions and assume configurations suited to transmit the rotary forces in the rotating direction. More specifically, as shown in, e.g., FIG. 22, the inner slide member 141 is formed to assume a cross in vertical section. The outer slide member 139 is formed with a hole of the same configuration adaptive to insertion of the inner slide member 141 as that of this member 141. Turning to FIG. 23, the inner slide member 141 may be formed in a square-pole-like shape. The outer slide member 139 may be formed with a hole of the same configuration as that of the inner slide member 141.

A rotary shaft 142 is connected to the front end of the inner slide member 141. The rotary shaft 142 penetrates the top part body 126 and protrudes outside from the opening for the treatment member. The rotary shaft 142 is so retained by two pieces of bearings 143, 143 as to be rotatable about the top part body 126. A spacer 144 is interposed between the two bearings 143, 143. A fixing ring 145 is fixed to an outer peripheral portion of the rotary shaft 142 in a position behind the bearing 143 closer to the rear end. The fixing ring 145 and a stepped portion of the rotary shaft 142 disposed in front of the bearing 143 closer to the front end cooperate to seize the bearings 143, 143 and the spacer 144. The rotary shaft 142 and the bearings 143, 143 are thus fixed.

An outside diameter, closer to the top end than the stepped portion, of the rotary shaft 142 is larger than the outside diameter closer to the rear end than the stepped portion. An internal thread is formed in the top end of the rotary shaft 142. Detachably screwed in this internal thread is an external thread 147 of a rotary treatment member 146 including a whetstone.

The front end of the protection tube 137 is connected via a pipe 148 to the top part body 126, while its rear end passes through the operating unit 109 and is led into the rotary driving section 103.

The image guide 133 and the light guide 135 are slackened as required in the operating unit 109 enough to make the top part body 126 slide along the bending part 123.

The operation of this embodiment will next be explained.

The top part body 126 of the top part 122 is slid on the cylindrical member 130, i.e., the bending part 123 in the axial direction. There is varied a length of a part closer to the top end than the bending part 123, viz., the length of the hard part including the top part body 126 and the cylindrical member 130. At this time, the projections 122a and 130a press against each other. Hence, the top part body 126 can be fixed in an arbitrary position with respect to the cylindrical member 130.

When grinding a damaged portion of a turbine blade 149 of the jet engine, as illustrated in FIG. 20, the insertion unit 108 of the endoscope 101 is inserted via an access port 150 into the jet engine. The electric power is supplied from the controller 105 to the rotary driving section 103 by depressing a fit switch 107. A motor housed in the rotary driving section 103 is thereby rotated. Rotary forces of the motor are transmitted via the flexible rotary force transmitting member 138 to the rotary shaft 142, thereby rotating the rotary treatment member 146. The damaged portion of the turbine blade 149 can be ground by the rotary treatment member 146.

In accordance with this embodiment, the top part 122 provided with the objective optical system 132 and the rotary treatment member 146 is slid along the bending part 123 in the axial directions. With this arrangement, the length of the hard part of the top part 122 can freely be changed. It is therefore possible to select the length of the hard top part with respect to the member to be processed as the blade 149 under optimum observing conditions. The treatment can be effected in an easy-to-observe state.

In this embodiment, the ocular unit 113 is disposed in such a way that the axis of the ocular unit 113 is inclined to an axis of the connecting member 112 (i.e., the axis of the insertion unit 108). As a result, the rotary driving section 103 can be disposed concentrically with the connecting member 112. Owing to this placement, the flexible rotary force transmitting member 138 can be made rectilinear in the vicinity of the rotary driving section 103. This creates a merit of preventing a frictional loss or abrasion caused by the bending placement. Note that in FIG. 20, the TV camera 115 may be connected directly to the connecting member 112.

FIG. 24 depicts the top part in a fifth embodiment of the present invention.

As shown in FIG. 24, in accordance with this embodiment, a circumferential groove 122b is furrowed in an outer periphery of the rear end portion of the top part body 126. A circumferential groove 128b is also furrowed in an outer periphery of the front end portion of the outermost bending piece 128a. A cylindrical holding member 160 is formed, at its front and rear ends, with engaging portions engaging with the grooves 122b and 128b. The outermost bending piece 128a is connected via this holding member 160 to the top part body 126.

Referring to FIGS. 25 and 26, the holding member 160 is constructed by connecting two semi-cylindrical members 161 and 162 to each other with hinges 163. An end portion 161a of the semi-cylindrical member 161 engages with an end portion 162a of the semi-cylindrical member 162 by pressing both members.

In this embodiment, a plurality of holding members 160 each having an arbitrary length are prepared. One of these members 160 is selected. The selected holding member 160 serves to connect the top part body 126 to the bending part 123.

As discussed above, in accordance with this embodiment, the length of the hard part closer to the top end than the bending part 123 can be varied by use of the holding member 160 having the arbitrary length.

Hence, the treatment can be carried out in the optimum observing state.

Other constructions, functions and effects are the same as those of the fifth embodiment.

Figure 27:
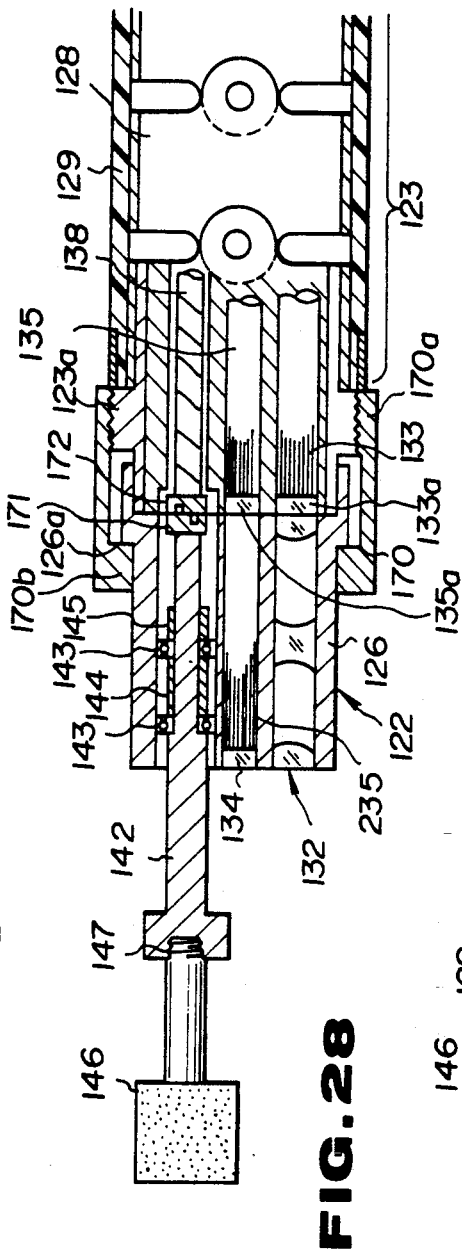
FIGS. 27 and 28 show a seventh embodiment of the invention.

FIG. 27 depicts the top part in a seventh embodiment of this invention.

In the seventh embodiment, a top part 122 having an arbitrary length is detachably fixed to the front end of the bending part 123.

As shown in FIG. 27, the top part 122 and the bending part 123 are formed separately. An external thread 123a is formed on an outer periphery of the front end portion of the bending part 123. Provided at the front end of the bending part 123 are a fitting member 172 secured to the top end of the rotary force transmitting member 138, a cover glass 133a joined to the top end face of the image guide 133 and a cover glass 135a joined to the top end face of the light guide 135.

The top part 122 includes the cylindrical top part body 126. The top part body 126 is formed with an observation through-hole, an illumination through-hole and a through-hole for a treatment member. The observation through-hole accommodates the objective optical system 132 for forming a subject image on the top end face of the image guide 133. The illumination through-hole accommodates the illumination optical system 134 on the top end side. A light guide 235 is provided at the rear end of the illumination optical system 134. The rear end face of the light guide 235 faces the cover glass 135a. In the through-hole for the treatment member, a rotary shaft 142 is rotatably retained by bearings 143, 143. Note that a spacer 144 is, as in the fifth embodiment, interposed between the bearings 143, 143. A fixing ring 145 is fixed to an outer peripheral portion of the rotary shaft 142 in a position behind the bearing 143 closer to the rear end thereof. A fitting member 171 fitted to the fitting member 172 is provided at the rear end of the rotary shaft 142. The fitting members 171 and 172 are fitted together to assume a configuration suited to transmit the rotary forces. A rotary treatment member 146 is attached to the front end of the rotary shaft 142.

A ring-like fixing member 170 is rotatably externally fitted to an outer periphery of the top part body 126. The fixing member 170 has a projection 170b provided at its front end to project inwards. A stepped portion is shaped on the outer periphery of the rear end portion of the top part body 126. A backward movement of the fixing member 170 is regulated by impingement of the projection 170b upon the stepped portion 126a. An internal thread 170a is formed in the rear end portion of the fixing member 170. An external thread 123a of the bending part 123 meshes with the internal threads 170a.

In this embodiment, the fixation of the top part 122 to the bending part 123 involves the following steps. The ring-like fixing member 170 is rotated in a state where the top part 123 is pressed against the front end of the bending part 123, as a result of which the fitting members 171 and 172 are fitted to each other. Then, the external thread 123a is engaged with the internal thread 170a. Incidentally, there are prepared the top parts 122 having a variety of arbitrary lengths.

Figure 28:
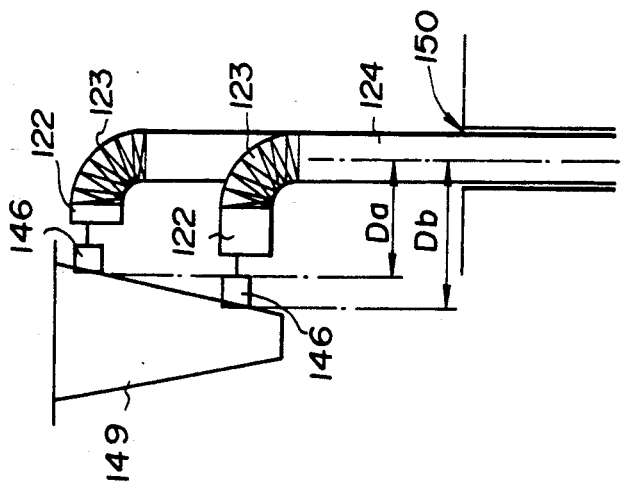

In accordance with this embodiment, as illustrated in FIG. 28, a length of the hard part closer to the top end than the bending part 123 can be varied by attaching the top part 122 having an arbitrary length to the bending part 123. Hence, even if a distance (Da, Db) from the central axis of the hard part 124 to a grinding position is changed depending on a shape of the turbine blade 149, the treatment can be performed under the optimum observing conditions.

Other constructions, functions and effects are the same as those of the fifth embodiment.

Next, two examples are given, wherein a length of the bendable portion of the bending part 123 is changed.

Figure 29:
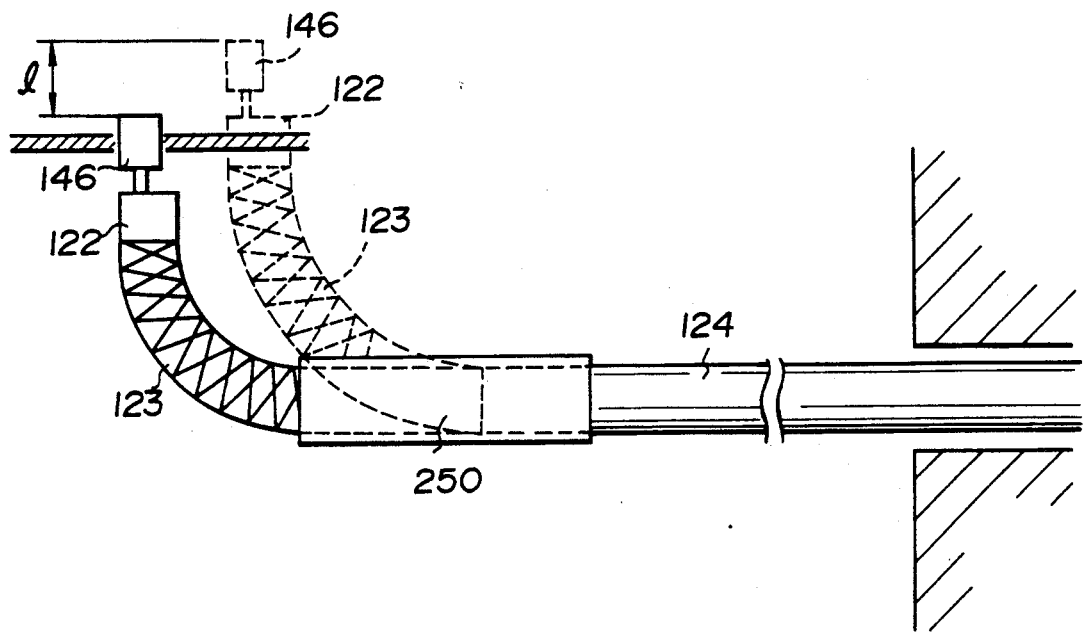
FIGS. 29 and 30 show an eighth embodiment of the invention.

Referring to FIG. 29, a hard cylindrical member 250 for regulating the bending action is provided at the rear or front end of the bending part 123. With this arrangement, the bendable portion of the bending part 123 is shortened. When bending the shortened bending part 123, a bending radius is reduced. In consequence, the rotary treatment member 146 varies in its position. To be specific, the distance from the central axis of the hard part 124 to the grinding position changes by 1.

As explained above, the provision of the cylindrical member 250 for regulating the bending action facilitates the change of a grindable range.

Figure 30:
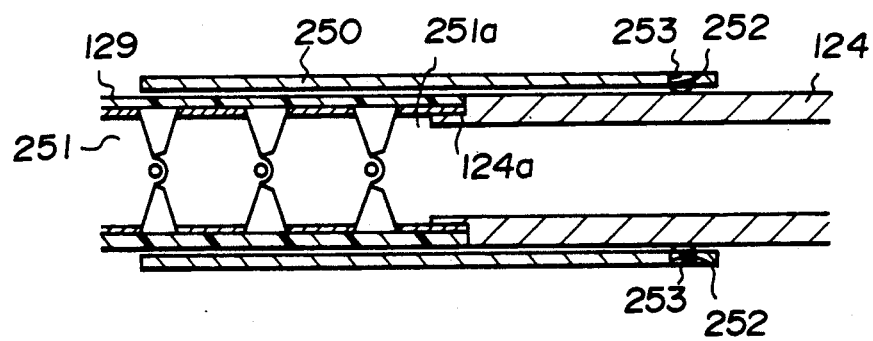

The cylindrical member 250 is fixed in the manner as shown in, e.g., FIG. 30. More specifically, the last piece 251a of a bending tube 251 constituting the bending part 123 is connectively fitted in a small-diameter portion 124a of the top end of the hard part 124. A sheath 129 is covered on the outer periphery of the bending tube 251. The cylindrical member 250 is fixed to the hard part 124 by inserting machine screws 253 into a plurality of screw holes 252 bored in the rear end thereof and pressing the hard part 124 with tips of the screws 253. When changing the portion for bending regulation, the machine screws 253 are slackened, and the cylindrical member 250 is shifted in the longitudinal direction. The screws 253 are again fastened.

Another example of the method of fixing the cylindrical member 250 will be demonstrated by FIGS. 31 and 32. In this example, as depicted in FIG. 31, a circumferential groove 124b are furrowed in an outer peripheral portion of the top end of the hard part 124. Fitted in the groove 124b in FIG. 32 is an elastic ring (C-shaped ring) partially formed with a notch 254a. A plurality of circumferential grooves 250a are furrowed in an inner peripheral face of the cylindrical member 250. The ring 254 is fitted in the groove 250a, thereby fixing the cylindrical member 250 to the hard part 124. Forces acting in the axial directions are applied to the cylindrical member 250, whereby the cylindrical member 250 changes in position with respect to the hard part 124.

FIGS. 33 and 34 shows still another example of the method of fixing the cylindrical member 250. In this example, as illustrated in FIG. 31, the rear end of the cylindrical member 250 is formed with an external thread 250b. The external thread 250b engages with an internal thread 255a formed in a fastening member 255. The fastening member 255 is connected to the cylindrical member 250. An elastic ring 256 having an elasticity is interposed between an ear end face 250e of the cylindrical member 250 and a front end face 255b of an projection projecting inwards and shaped on the rear end of the fastening member 255. When the fastening member 255 is screwed into the rear end of the cylindrical member 250, the fastening member 255 presses the elastic ring 256. The pressed elastic ring 256 is, as illustrated in FIG. 34, expanded in the radial directions. As a result, there are pressed an inner periphery 255c of the rear end portion of the cylindrical member 250 and the outer periphery of the hard part 124. The cylindrical member 250 and the hard part 124 are thus fixed. A stepped portion 124c is shaped at the front end of the hard part 124. A stepped portion 250d is formed in the inner periphery of the cylindrical member 250. The stepped portions 124c and 250d get caught each other to thereby prevent the cylindrical member 250 from coming off towards the top end of the insertion unit, even when the engagement of the external thread 250b with the internal thread 255a is released during the employment.

Other constructions, functions and effects of this embodiment are the same as those of the fifth embodiment.

Figure 35:
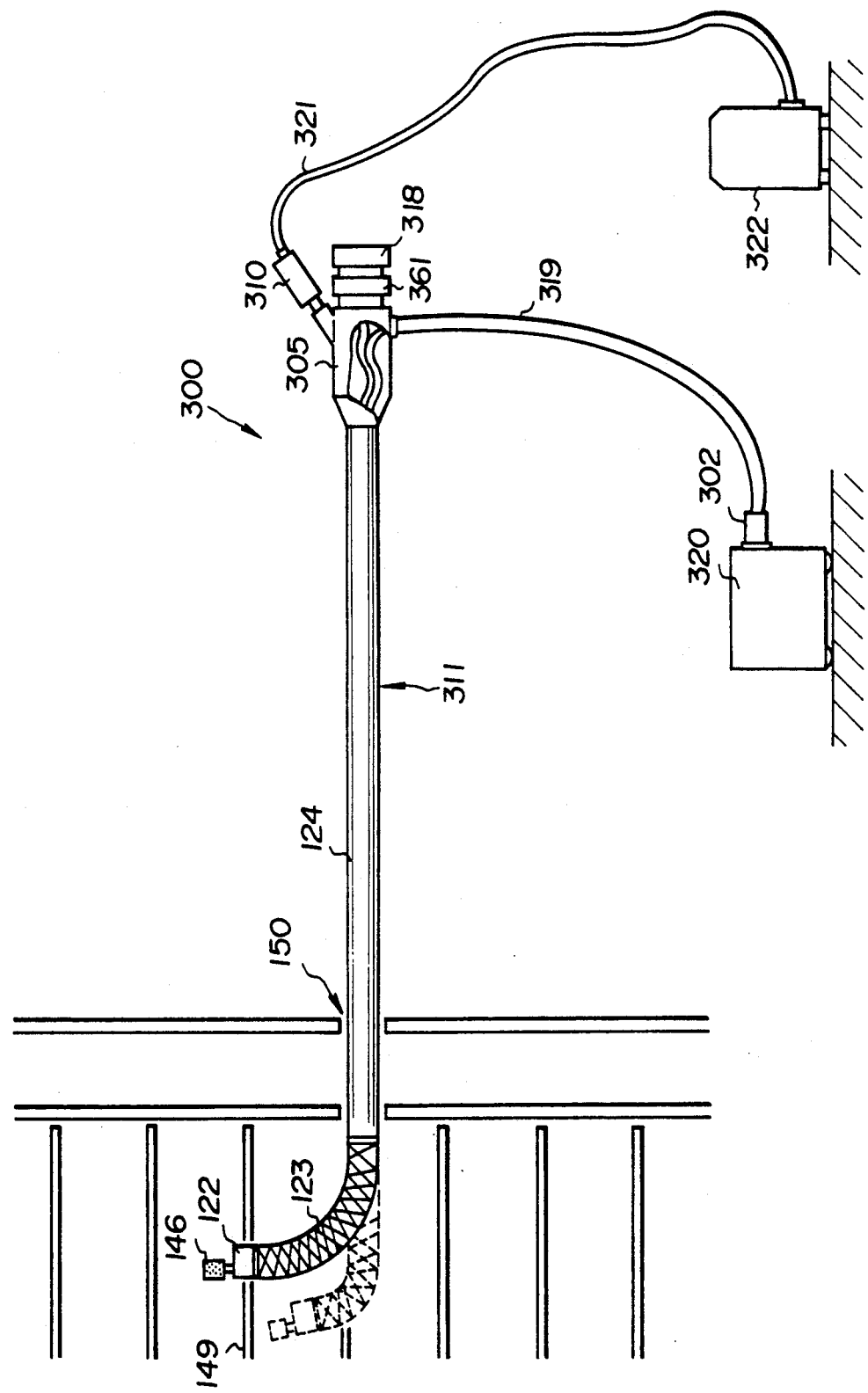
FIGS. 35 through 37 show a ninth embodiment of the invention.

A ninth embodiment of this invention is demonstrated by FIG. 35.

In the ninth embodiment also, a bendable length of the bending part is variable.

An industrial endoscope system 300 depicted in FIG. 35 comprises: an endoscope 301 (for engineering); a light source apparatus 320 connected to the endoscope 301; a rotary driving section 310 connected to the endoscope 301; and a controller 322 connected via a cord 321 to the rotary driving section 310.

The endoscope 301 includes: an elongate insertion unit 311; an operating unit 305 provided in continuation from the rear end of the insertion unit 311; and a universal cord 319 extending sideways from the operating unit 305. A connector 302 detachably connected to a light source apparatus 320 is provided at the rear end of the universal cord 319. An ocular unit 318 is disposed at the rear end of the operating unit 305.

The insertion unit 311 is composed of, sequentially from its top end, the hard top part 122, the bendable bending part 123 and the hard part 124.

Figure 36:
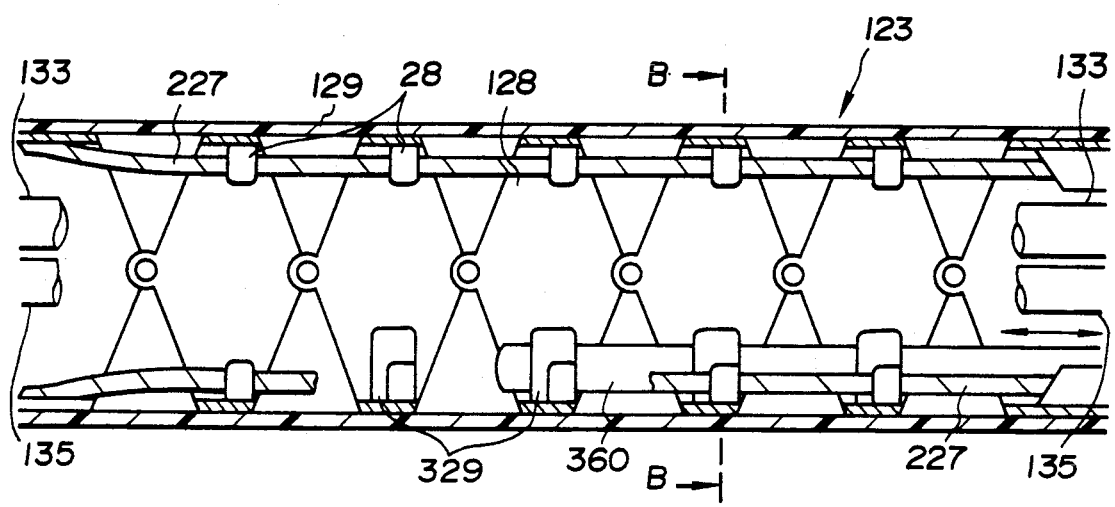
Figure 37:
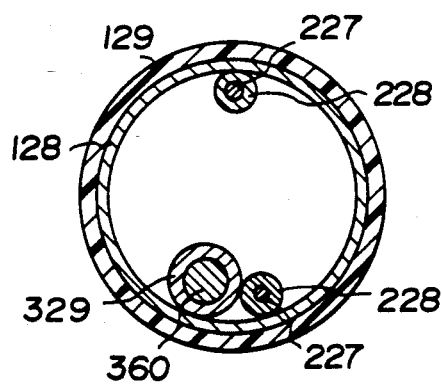

A bending length adjusting ring 361 is provided at the rear end of the operating unit 305. The bending length adjusting ring 361 is connected to a hard bar-like bending length adjusting member 360 inserted into a hard part 124. The bending length adjusting member 360 is shifted in the axial directions by rotating the adjusting ring 361. As illustrated in FIGS. 36 and 37, the bending pieces 128 incorporate a guide 329 into which the adjusting member 360 is inserted.

Note that the numeral 227 designates a wire used for bending the bending part 123. When rotationally manipulating an unillustrated bending operation knob in the operating unit 305, one of a pair of wires 227, 227 is pulled, whereas the other is slackened. It follows that the bending parts 123 is bent towards the pulled wire 227.

In this embodiment, the bending length adjusting ring 361 is rotated in one direction. At this time, the front end of the bending length adjusting member 360 passes through the guide 329 and is extruded towards the top end. When rotating the adjusting ring 361 in the reverse direction, the adjusting member 360 is pulled back to the operating unit 305. In the bending part 123, the portion at which the adjusting member 360 is formed is not bent. The adjusting member 360 is thrust or pulled by turning the adjusting ring 361, whereby, as illustrated in FIG. 35, a length of the bendable portion of the bending part 123 can arbitrarily be changed. A rotary treatment member 146 is led to a desired position, wherein the treatment can be effected.

Other constructions, functions and effects are the same as those of the fifth embodiment.

According to the fifth through ninth embodiments, there is provided is the means for changing the length of the hard part of the insertion unit. This produces an advantage of performing the treatment in a desired position while keeping the observing state constant.

Figure 38:
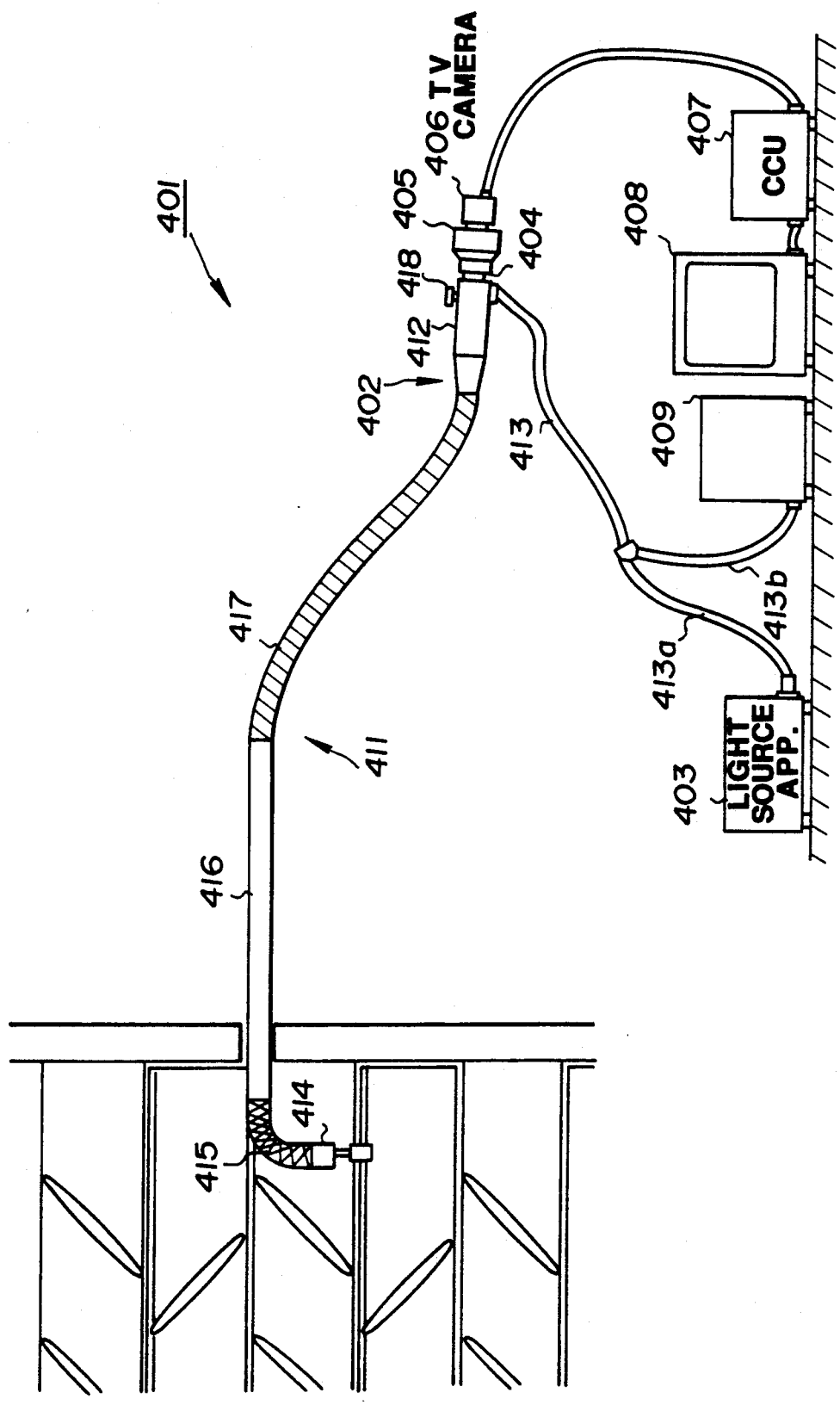

FIG. 38 shows a tenth embodiment of this invention.

In the tenth embodiment, the rotary treatment member is rotated by use of a Pelton turbine as a rotary driving source.

An endoscope 401 comprises a fiber scope 402, a light source apparatus 403, a TV camera 406, a CCU 407, a monitor 408 and a pressurizing fluid source 409. The light source apparatus 403 supplies the fiber scope 402 with the illumination light. The TV camera 406 is mounted via an adaptor 405 on an ocular unit 404 of the fiber scope 402. The CCU 407 processes the signals to the TV camera 406. The monitor 408 is connected to the CCU 407. The pressurizing fluid source 409 feeds out a pressurizing fluid for rotational driving.

The fiber scope 402 is constructed of: an insertion unit 411; an operating unit 412 formed at the rear end of the insertion unit 411; an ocular unit 404 shaped at the rear end of the operating unit 412; and a universal cord 413 extending from the operating unit 412. The universal cord 413 is branched off midways into two cords 413a and 413b connected to the light source apparatus 403 and the pressurizing fluid source 409, respectively.

The insertion unit 411 consists of a hard top part provided at the top end (terminal), a bending part 415, a hard part 416 and a soft part 417. The bending part 412 is bendable vertically or laterally by operating a bending knob 418 attached to the operating unit 412. The soft part 417 is constructed of, e.g., an interlock type helical tube.

Inserted into the insertion unit 411 in FIG. 39 are a light guide 421, an image guide 422 and a (fluid) feeding tube 423.

The light guide 421 leading from the operating unit 412 passes through the cords 413 and 413a and is connected to the light source apparatus 403. The light guide 421 transmits the illumination light emerging from the light source apparatus 403. The illumination light is emitted after traveling through an illumination optical system 424 as well as through an end face fixed to a hard top part 414. A subject (for inspection) is illuminated with the illumination light emitted via the illumination optical system 424. An image of this subject is formed on a top end face of the image guide 422 by means of an objective optical system 425 incorporated into the hard top part 414. The image is transmitted through the image guide 422 to the end face of the ocular unit 404. Then, an imaging process is carried out in the TV camera 406. The subject image (endoscope image) is displayed on a display screen of the monitor 408.

In the hard top part 414, a substantially cylindrical slider 430 is movably fitted into a through-hole formed adjacently to the objective optical system 425. In a recess formed in the slider 430, the runner 426 is rotatably retained by the bearings 427, 427. A screw 426b is provided at the front end of a shaft of the runner 426. The screw 426b engages with a screw 428a formed at the rear end of a connecting shaft 428.

Engaged with a screw 428b formed at the front end of the connecting shaft 428 is a screw 432a of a rotary shaft 432 of a rotary treatment member 431. The rotary treatment member 431 is detachably fixed to the connecting shaft 428.

The pressurizing fluid source 409 is connected via the cords 413 and 413b to the rear end of the feeding tube 423. A pressurizing fluid is thus fed out from the pressurizing fluid source 409. The pressurizing fluid source 409 is composed of a pneumatic cylinder, a nitrogen gas cylinder and a compressor.

The front end of the tube 423 is connected to a connecting pipe 434 attached to the rear end of a fluid passageway 433 formed in the slider 430. The fluid passageway 433 extends to a front end face 414a of the slider 430. The passageway 433 is bent in a position vicinal to the center of the runner 426, thus forming an ejection port 435 for ejecting the fluid to the runner 426. FIG. 40 depicts a sectional structure of this part.

Referring to FIG. 40, the hard top part 414 is formed with a discharge port 436 for discharging the fluid.

As illustrated in FIG. 39, the bending part 415 consists of a multiplicity of bending pieces 437, 437, . . . , the outer periphery of which is covered with a sheath 438. The top end of the wire 454 is connected to the rear end of the slider 430. The portion, on this side, of the wire 454 is shifted back and forth, whereby the rotary treatment member 431 can be shifted together with the slider 430 in the arrowed axial directions of the insertion unit 411.

The following is a description of a rotational operation of the rotary treatment member 431 in the tenth embodiment.

After feeding the fluid from the pressurizing fluid source 409 into the feeding tube 423, the fluid is ejected in the arrowed direction of FIG. 40 from the ejection port 435 in the hard top part 414. The ejected fluid impinges upon the blade 426a of the runner 426, thereby rotating the runner 426. The rotations of this runner are transmitted via the connecting shaft 428 to the rotary treatment member 431, as a consequence of which the member 431 is rotated.

Omitted herein a description of such a treatment that the rotary treatment member 431 polishes a damaged portion of the blade in the jet engine. Because this has been stated before.

The tenth embodiment exhibits the following effects.

The fluid is employed for rotating the rotary treatment member 431. There is no necessity for inserting, into the bending part 415, a relatively hard member like the flexible shaft having a considerable strength enough to transmit the rotary forces. For this reason, the components such as the light guide 421, the image guide 422 and the like built in the bending part 415 are effectively prevented from being damaged due to the pressing forces (when inserting no flexible shaft). The bending part 415 can be bent with a small radius of curvature. The rotary treatment member 431 and the hard top part 414 can be set in desired positions. This facilitates the treatment such as grinding and the like.

FIG. 41 is a representation of the top part of the insertion unit of a fiber scope 402′ in an eleventh embodiment.

In the eleventh embodiment, an axial-flow turbine is used as a rotary driving source. A rotary treatment member fitted to the endoscope is rotationally driven by this turbine.

The front end of a tube 423 inserted into the insertion unit 411 is fixed to the connecting pipe 434 attached to the rear end of a through-hole bored in the hard top part 414.

This through-hole accommodates a pipe 451 slidable in the axial direction of the insertion unit 411. In this pipe 451, the bearings 427, 427 rotatably support the runner 426 including a plurality of blades 426a, . . . disposed at arbitrary angles inclined to the axial direction of the insertion unit 411.

Fixed within the pipe 451, as is also shown in FIG. 42, is a guide member 442 having a plurality of guide blades 441, . . . to confront the runner 426.

The guide blades 441, . . . are disposed at angles inclined to the axial direction of the runner 426. A flow-direction of the fluid is changed by the blades 441, . . . The fluid impinges on the blades 426a, . . . of the runner 426, thus incrementing the torque to rotate the runner 426.

A pin 452 protrudes from the pipe 451. The pin 452 is fitted in a guide groove furrowed in the hard top part 414 so that the pine 452 is movable in the longitudinal direction of the groove 453. Fixed to this pin 452 is one end of a wire 454 inserted into the insertion unit 411. The other end of the wire 454 protrudes (not illustrated) from the operating unit. The wire is moved to and fro, thereby moving the rotary treatment member 431 back and forth together with the runner 426 and the pipe 451 as well. A fixation with a positioning screw or the like (not shown) is effected to prevent further to-and-fro movements of the wire 454 from a state where the wire 454 has been moved back and forth.

Note that the pipe 451 is bored with an opening 455 communicating with the discharge port 436 formed in the hard top part 414.

Other constructions are the same as those of the eleventh embodiment.

In this embodiment, as in the way with the tenth embodiment, the rotary treatment member 431 is moved to and fro (in the axial directions of the insertion unit) by operating the wire 454, which in turn facilitates the treatment such as grinding and the like. Provision of the fluid passageway 433 shown in the tenth embodiment is not required, and hence the hard top part 414 can be reduced in diameter.

It should be noted that in the respective embodiments discussed above, the rotary treatment member is not limited to the whetstone. The rotary treat member may include a file and a drill. In short, the requirement is such that the member grinds or polishes or cuts the contact target by rotating this member.

Different embodiments may be provided by partially combining the above-described embodiments.

Although the illustrative embodiment have been described in detail with reference to the accompanying drawings, it is to be understood that the present invention is not limited to those embodiments. Various changes or modifications may be effected by one skilled in the art without departing from the scope or spirit of the invention.

What is claimed is:

1. An industrial endoscope system comprising:
    (a) an industrial endoscope;
    an insertion unit having a hard top part formed of a hard material and a bendable bending part shaped at the rear end of said hard top part,
    an operating unit formed at the proximal end of said insertion unit and having a bend-operating means for bend-operating said bending part,
    an objective optical system, provided in said hard top part, for forming an optical image of an object,
    an illumination light emitting means, provided in said hard top part, for emitting the illumination light, and
    a rotary treatment member, provided to project from said hard top part, for effecting a treatment such as grinding, (b) a rotary driving means for rotationally driving said rotary treatment member; and (c) a moving means at least for making a distal end of said rotary treatment member movable in axial directions of said insertion unit.

2. The endoscope system as set forth in claim 1, wherein said illumination light emitting means is composed of a light guide means, inserted into said insertion unit of said industrial endoscope, for transmitting the illumination light supplied to its one end and emitting the illumination light from the other end fixed to said hard top part.

3. The endoscope system as set forth in claim 1, further comprising a light source means for supplying the illumination light to said one end of said light guide means.

4. The endoscope system as set forth in claim 1, wherein said illumination light emitting means consists of a lamp, provided in said hard top part, for emitting the illumination light.

5. The endoscope system as set forth in claim 1, wherein said rotary treatment member includes a rotary force transmitting member for transmitting rotary forces given by said rotary driving means and a grinding member, attached to a distal end of said rotary force transmitting means, for grinding a contact portion by rotating said grinding means itself.

6. The endoscope system as set forth in claim 5, wherein said grinding means is fixed in the vicinity of said rotary force transmitting member by an attachable/detachable fixing means.

7. The endoscope system as set forth in claim 6, wherein said fixing means is composed of a screw.

8. The endoscope system as set forth in claim 5, wherein said grinding means is fitted eccentrically with the central axis of said hard top part.

9. The endoscope system as set forth in claim 8, wherein said grinding means is attached to protrude outwards from an outside diameter of said hard top part in the radial direction.

10. The endoscope system as set forth in claim 5, wherein said rotary force transmitting member is composed of: a hard shaft member having a distal end fitted with said grinding member and its vicinity which are made of a hard member; and a flexible shaft connected to the proximal end of said hard shaft member.

11. The endoscope system as set forth in claim 10, wherein said hard shaft member has an outside diameter substantially equal to an inside diameter of a through-hole bored in said hard top part and is slidably insertable into said through-hole.

12. The endoscope system as set forth in claim 10, wherein said flexible shaft is slidably insertable into said through-hole.

13. The endoscope system as set forth in claim 5 or 10, wherein said rotary force transmitting member is inserted into said insertion unit and has its proximal end connected to said rotary driving means.

14. The endoscope system as set forth in claim 1 or 5, wherein a moving operation means of said moving means is provided in the vicinity of said operating unit.

15. The endoscope system as set forth in claim 1, wherein said industrial endoscope is a fiber scope having one end face disposed on a focal plane of said objective optical system and the other end face provided with an image guide for transmitting an optical image.

16. The endoscope system as set forth in claim 15, wherein said fiber scope incorporates a TV camera including an image forming optical system, mounted on an ocular unit formed on the other end face of said image guide, for forming the transmitted optical image on said other end face and a solid state imaging element disposed in an optical-image-forming position and having a photoelectric converting function.

17. The endoscope system as set forth in claim 1, wherein said industrial endoscope is an electronic scope in which a solid state imaging element having a photoelectric converting function is disposed on a focal plane of said objective optical system.

18. The endoscope system as set forth in claim 1, said rotary driving means consists of a rotary blade means connected to a distal end of said rotary treatment member, a fluid passageway means, formed in said insertion unit, for flowing said fluid and a fluid supply means for supplying said fluid via said fluid passageway means to said rotary blade means.

19. The endoscope system as set forth in claim 18, wherein said moving means makes said rotary treatment means movable by moving a ire inserted into said insertion unit in the axial directions of said insertion unit.

20. An industrial endoscope system, comprising:
(a) an industrial endoscope;
an insertion unit having a hard top part formed of a hard material and a bendable bending part shaped at the rear end of said hard top part,
an operating unit formed at the proximal end of said insertion unit and having a bend-operating means for bend-operating said bending part,
an objective optical system, provided in said hard top part, for forming an optical image of an object,
an illumination light emitting means, provided in said hard top part, for emitting the illumination light, and
a rotary treatment member, provided to project from said hard top part, for effecting a treatment such as grinding, wherein said rotary treatment member includes a rotary force transmitting member for transmitting rotary forces given by said rotary driving means and a grinding member, attached to a distal end of said rotary force transmitting means, for grinding/polishing/-grinding a contact portion by rotating said grinding means itself, and wherein said rotary force transmitting member is composed of: a hard shaft member having a distal end fitted with said grinding member and its vicinity which are made of a hard member; and a flexible shaft connected to the proximal end of said hard shaft member;
(b) a rotary driving means for rotationally driving said rotary treatment member; and
(c) a moving means at least for making a distal end of said rotary treatment member movable in axial directions of said insertion unit, wherein a moving operation means of said moving means is provided in the vicinity of said operating unit and makes said grinding member movable in the axial directions of said insertion unit by changing a bending quantity of said flexible shaft vicinal to said operating unit.

21. An industrial endoscope system, comprising:
(a) an industrial endoscope;
an insertion unit having a hard top part formed of a hard material and a bendable bending part shaped at the rear end of said hard top part, an operating unit formed at the proximal end of said insertion unit and having a bend-operating means for bend-operating said bending part, an objective optical system, provided in said hard to part, for forming an optical image of an object, an illumination light emitting means, provided in said hard top part, for emitting the illumination light, and a rotary treatment member, provided to project from said hard top part, for effecting a treatment such as grinding, wherein said rotary treatment member includes a rotary force transmitting member for transmitting rotary forces given by said rotary driving means, and a grinding member, attached to a distal end of said rotary force transmitting means, for grinding/polishing/grinding a contact portion by rotating said grinding means itself, and wherein said rotary force transmitting member is composed of: a hard shaft member having a distal end fitted with said grinding member and its vicinity which are made of a hard member; and a flexible shaft connected to the proximal end of said hard shaft member;

(b) a rotary driving means for rotationally driving said rotary treatment member; and (c) a moving means at least for making a distal end of said rotary treatment member movable in axial directions of said insertion unit, wherein a moving operation means of said moving means is provided in the vicinity of said operating unit and operates to move, together with said flexible shaft, said rotary driving means connected to the proximal end of said flexible shaft.

22. An industrial endoscope system, comprising:
(an) an industrial endoscope;
   an insertion unit having a hard top part formed of a hard material and an bendable bending part shaped at the rear end of said hard top part,
   an operating unit formed at the proximal end of said insertion unit and having a bend-operating means for bend-operating said bending part,
   an objective optical system, provided in said hard top part, for forming an optical image of an object,
   an illumination light emitting means, provided in said hard top part, for emitting the illumination light, and
   a rotary treatment member, provided to project from said hard top part, for effecting a treatment such as grinding;

(b) a rotary driving means for rotationally driving said rotary treatment member; and (c) a moving means at least for making a distal end of said rotary treatment member movable in axial directions of said insertion unit, wherein said moving means makes movable said distal end of said hard top part to which a distal end of said rotary treatment member is attached with respect to a proximal end of said hard top part, and said moving means also makes said distal end of said rotary treatment member movable in the axial directions of said insertion unit together with said distal end of said hard top part.

23. An industrial endoscope system, comprising:
(a) an industrial endoscope;
   an insertion unit having a hard top part formed of a hard material and a bendable bending part shaped at the rear end of said hard top part, wherein said bending part has a bendable length variable by inserting a hard moving member from a proximal end of said bending part,
   an operating unit formed at the proximal end of said insertion unit and having a bend-operating means for bend-operating said bending part,
   an objective optical system, provided in said hard top part, for forming an optical image of an object,
   an illumination light emitting means, provided in said hard top part, for emitting the illumination light, and
   a rotary treatment member, provided to project from said hard top part, for effecting a treatment such as grinding;

(b) a rotary driving means for rotationally driving said rotary member; and (c) a moving means at least for making a distal end of said rotary treatment member movable in axial directions of said insertion unit.

* * * * *

UNITED STATES PATENT AND TRADEMARK OFFICE
CERTIFICATE OF CORRECTION

PATENT NO. : 5,155,941

DATED : October 20, 1992

INVENTOR(S) : Ichiro TAKAHASHI et al.

It is certified that error appears in the above-identified patent and that said Letters Patent is hereby corrected as shown below:

On the cover page, Item [75], line 2, "Tatami" should read --Tagami--.

Signed and Sealed this

Twenty-third Day of November, 1993

Attest:

BRUCE LEHMAN

*Attesting Officer*   *Commissioner of Patents and Trademarks*